(12) United States Patent
Arambula et al.

(10) Patent No.: US 11,332,483 B2
(45) Date of Patent: May 17, 2022

(54) NAPHTHOQUINONE CONTAINING GOLD CARBENE COMPLEXES AND METHODS OF USES THEREOF

(71) Applicants: BOARD OF REGENTS, THE UNIVERSITY OF TEXAS SYSTEM, Austin, TX (US); GEORGIA SOUTHERN UNIVERSITY, Statesboro, GA (US); WRIGHT STATE UNIVERSITY, Dayton, OH (US)

(72) Inventors: Jonathan Arambula, Pooler, GA (US); Kuppuswamy Arumugam, Dayton, OH (US); Jonathan L. Sessler, Austin, TX (US); Christopher Bielawski, Ulsan (KR)

(73) Assignees: BOARD OF REGENTS, THE UNIVERSITY OF TEXAS SYSTEM, Austin, TX (US); GEORGIA SOUTHERN UNIVERSITY, Statesboro, GA (US); WRIGHT STATE UNIVERSITY, Dayton, OH (US)

( * ) Notice: Subject to any disclaimer, the term of this patent is extended or adjusted under 35 U.S.C. 154(b) by 0 days.

(21) Appl. No.: 16/625,023

(22) PCT Filed: Jun. 29, 2018

(86) PCT No.: PCT/US2018/040331
§ 371 (c)(1),
(2) Date: Dec. 20, 2019

(87) PCT Pub. No.: WO2019/006327
PCT Pub. Date: Jan. 3, 2019

(65) Prior Publication Data
US 2020/0216473 A1 Jul. 9, 2020

Related U.S. Application Data

(60) Provisional application No. 62/527,606, filed on Jun. 30, 2017.

(51) Int. Cl.
*C07F 1/00* (2006.01)
*A61P 35/00* (2006.01)

(52) U.S. Cl.
CPC ............... *C07F 1/00* (2013.01); *A61P 35/00* (2018.01)

(58) Field of Classification Search
CPC .................................. A61P 35/00; C07F 1/00
See application file for complete search history.

(56) References Cited

PUBLICATIONS

"Development of redox active N-heterocyclic carbenes to alter the metabolism of reactive oxygen species in biological systems", Baylor University presentation 2015.

(Continued)

*Primary Examiner* — Jianfeng Song
(74) *Attorney, Agent, or Firm* — Parker Highlander PLLC

(57) ABSTRACT

The present disclosure relates gold carbene naphthoquinone compounds and salts thereof. In some aspects, these compounds can be used to treat cancer including cancers which are resistant to one or more other chemotherapeutic agents such as cisplatin or platinum chemotherapeutic agents. Also provided herein are pharmaceutical compositions comprising the gold carbene naphthoquinone compounds.

11 Claims, 12 Drawing Sheets

(56) References Cited

PUBLICATIONS

"Development of redox active N-heterocyclic carbenes to alter the metabolism of reactive oxygen species in biological systems", Texas Christian University presentation 2015.

"Development of redox active N-heterocyclic carbenes to alter the metabolism of reactive oxygen species in biological systems", Texas Slate presentation 2015.

Arambula, J. F., et al. "Targeting antioxidant pathways with ferrocenylated N-heterocyclic carbene supported gold (I) complexes in A549 lung cancer cells." *Chemical science* 7.2 (2016): 1245-1256.

Aranzaes, Jaime Ruiz, Marie-Christine Daniel, and Didier Astruc. "Metallocenes as references for the determination of redox potentials by cyclic voltammetry Permethylated iron and cobalt sandwich complexes, inhibition by polyamine dendrimers, and the role of hydroxy-containing ferrocenes." *Canadian journal of chemistry* 84.2 (2006): 288-299.

Barnard, Peter J., et al. "Dinuclear gold (I) complexes of bridging bidentate carbene ligands: synthesis, structure and spectroscopic characterisation." *Dalton Transactions* 7 (2004): 1038-1047.

De Frémont, Pierre, et al. "Synthesis and structural characterization of N-heterocyclic carbene gold (I) complexes." *Organometallics* 24.10 (2005): 2411-2418.

Fako, Valerie E., and Darin Y. Furgeson. "Zebrafish as a correlative and predictive model for assessing biomaterial nanotoxicity." *Advanced drug delivery reviews* 61.6 (2009): 478-486.

Gómez, Martin, et al. "The association of neutral systems linked by hydrogen bond interactions: a quantitative electrochemical approach." *Electrochemistry communications* 5.1 (2003): 12-15.

Guin, Partha Sarathi, Saurabh Das, and P. C. Mandal. "Electrochemical reduction of quinones in different media: a review." *International Journal of Electrochemistry* 2011 (2011).

Hashmi, A. Stephen K., et al. "New and Easily Accessible Nitrogen Acyclic Gold (I) Carbenes: Structure and Application in the Gold-Catalyzed Phenol Synthesis as well as the Hydration of Alkynes." *Advanced Synthesis & Catalysis* 352.8 (2010): 1315-1337.

He, Ningning, et al. "Exploring the toxicity of a bismuth-asparagine coordination polymer on the early development of zebrafish embryos." *Chemical Research in Toxicology* 26.1 (2013): 89-95.

Heimberger, Julia, et al. "Total synthesis of Herbarin A and B, determination of their antioxidant properties and toxicity in zebrafish embryo model." *Bioorganic & Medicinal Chemistry Letters* 25.6 (2015): 1192-1195.

Hill, Adrian J., et al. "Zebrafish as a model vertebrate for investigating chemical toxicity." *Toxicological sciences* 86.1 (2005): 6-19.

Hu, Xile, et al. "Group 11 metal complexes of N-heterocyclic carbene ligands: nature of the metal carbene bond." *Organometallics* 23.4 (2004): 755-764.

International Preliminary Report on Patentability issued in International Application No. PCT/US2018/040331, dated Jan. 9, 2020.

International Search Report and Written Opinion issued in International Application No. PCT/US2018/040331, dated Sep. 27, 2018.

Iqbal, Mohammad S., et al. "In vitro distribution of gold in serum proteins after incubation of sodium aurothiomalate and auranofin with human blood and its pharmacological significance." *Biological trace element research* 130.3 (2009): 204-209.

Jung, Da-Woon, et al. "A novel zebrafish human tumor xenograft model validated for anti-cancer drug screening." *Molecular BioSystems* 8.7 (2012): 1930-1939.

Kalyanaraman, B. "Nitrated lipids: a class of cell-signaling molecules." *Proceedings of the National Academy of Sciences* 101.32 (2004): 11527-11528.

Konantz, Martina, et al. "Zebrafish xenografts as a tool for in vivo studies on human cancer." *Annals of the New York Academy of Sciences* 1266.1 (2012): 124-137.

Poornima, Paramasivan, et al. "Doxorubicin induced apoptosis was potentiated by neferine in human lung adenocarcima, A549 cells." *Food and chemical toxicology* 68 (2014): 87-98.

Roberts, Jacqueline R., et al. "Kinetics and mechanism of the reaction between serum albumin and auranofin (and its isopropyl analogue) in vitro." *Inorganic chemistry* 35.2 (1996): 424-433.

Sanderson, Matthew D., Justin W. Kamplain, and Christopher W. Bielawski. "Quinone-annulated N-heterocyclic carbene—transition-metal complexes: observation of π-backbonding using FT-IR spectroscopy and cyclic voltammetry." *Journal of the American Chemical Society* 128.51 (2006): 16514-16515.

Santoro, Orlando, et al. "Homoleptic and heteroleptic bis-NHC Cu (I) complexes as carbene transfer reagents," *Dalton Transactions* 45.12 (2016): 4970-4973.

Sittaramane, Vinoth, et al. "Discovery of Quinoline-Derived Trifluoromethyl Alcohols, Determination of Their in vivo Toxicity and Anticancer Activity in a Zebrafish Embryo Model." *ChemMedChem* 10.11 (2015): 1802-1807.

Stordal, Britta, and Mary Davey. "Understanding cisplatin resistance using cellular models." *IUBMB life* 59.11 (2007): 696-699.

Tennyson, Andrew G., Vincent M. Lynch, and Christopher W. Bielawski. "Arrested Catalysis: Controlling Kumada Coupling Activity via a Redox-Active N-Heterocyclic Carbene." *Journal of the American Chemical Society* 132.27 (2010): 9420-9429.

Tucker, Ben, and Michael Lardelli. "A rapid apoptosis assay measuring relative acridine orange fluorescence in zebrafish embryos." *Zebrafish* 4.2 (2007): 113-116.

Veinotte, Chansey J., Graham Dellaire, and Jason N. Berman. "Hooking the big one: the potential of zebrafish xenotransplantation to reform cancer drug screening in the genomic era." *Disease models & mechanisms* 7.7 (2014): 745-754.

Wang, Harrison MJ, and Ivan JB Lin. "Facile synthesis of silver (I)-carbene complexes. Useful carbene transfer agents." *Organometallics* 17.5 (1998): 972-975.

Westerfield, The Zebrafish Book. A Guide for the Laboratory Use of Zebrafish (*Danio rerio*), 4th ed.; University of Oregon Press: Eugene, 2000. Downloaded from https://zfin.org/zf_info/zfbook/zfbk.html on Dec. 19, 2020.

Xie, Xiayang, et al. "Suppression of breast cancer metastasis through the inactivation of ADP-ribosylation factor 1." *Oncotarget* 7.36 (2016): 58111.

Zhang, Jingpu, et al. "Toxic effects of cephalosporins with specific functional groups as indicated by zebrafish embryo toxicity testing." *Chemical research in toxicology* 26.8 (2013): 1168-1181.

NAPHTHOQUINONE CONTAINING GOLD CARBENE COMPLEXES AND METHODS OF USES THEREOF

This application is a national phase application under 35 U.S.C. § 371 of International Application No. PCT/US2018/040331, filed Jun. 29, 2018, which claims the benefit of priority to U.S. Provisional Application No. 62/527,606, filed on Jun. 30, 2017, the entire contents of each of which are hereby incorporated by reference.

This invention was made with government support under Grant Number R01 CA068682 awarded by the National Institutes of Health. The government has certain rights in the invention.

BACKGROUND

1. Field

The present disclosure relates generally to the fields of medicine, pharmaceutical agents, and chemotherapeutics. The present disclosure relates to gold carbene napthaquinone complexes and compositions, which can be used to treat cancer.

2. Description of Related Art

Recently, a wide variety of different metal based chemotherapeutic agents have been used to treat cancers including, but not limited to lung cancer, breast cancer, esophageal cancer, brain cancer, bladder cancer, testicular cancer, head and neck cancer, cervical cancer, and ovarian cancer. Given the wide use of these therapeutic agents in a range of possible cancers, the cancer cell lines can develop resistance to these chemotherapeutic agents with their repeated use. For example, several cell lines such as ovarian cancer, have already become resistant to platinum therapeutic agents are referred to as platinum refractory cancers. Some initial research has shown that platinum refractory cancer cells are often associated with changes in the cellular stress response (Stordal and Davey, 2007). Often, this refractory status is conferred by development of one or more mutations in TP53 enzyme and methods to restore TP53 activity help to resensitize the cell towards platinum therapeutics. While these methods restore some level of activity in platinum refractory cancer cell lines, these combinations often do not achieve similar activity to non-refractory cancer cell lines.

Additionally, many therapeutic agents target a single biological effector which often results in only marginal or weak biological effect. On the other hand, there is growing interest in dual therapeutic agents which can both target a single biological effector as well as act on the entire pathway to reduce the ability of redundant pathways to achieve the same biological expression. In particular, within cancer, there is some interest in developing an agent which can both lead to an increase of reactive oxygen species as well as reduce the threshold of reactive oxygen species tolerance within a single cell. By effecting both elements, the combined therapy both reduces the amount of reactive oxygen species needed to kill the target cell as well as increase the production of those same species leading to an increased likelihood of achieving therapeutic effectiveness.

Therefore, the development of therapeutic agents which achieve multiple biological effects within a single biological pathways but are less susceptible to resistant by reducing the dependent or bypassing the TP53 enzyme are of commercial interest.

SUMMARY

In some aspects, the present disclosure provides compounds of the formula:

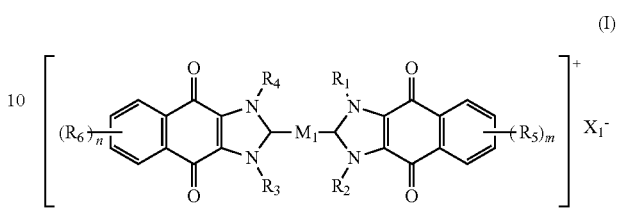

(I)

wherein:
  $M_1$ is an Au or Ag ion;
  $R_1$, $R_2$, $R_3$, and $R_4$ are each independently alkyl$_{(C \leq 12)}$, cycloalkyl$_{(C \leq 12)}$, aryl$_{(C \leq 18)}$, aralkyl$_{(C \leq 18)}$, or a substituted version of any of these groups; or —$(CR_aR_b)C(O)Y_1$; wherein:
    $Y_1$ is amino, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$, and
    $R_a$ and $R_b$ are each independently the side chain of a canonical amino acid or alkyl$_{(C \leq 8)}$, cycloalkyl$_{(C \leq 8)}$, aryl$_{(C \leq 12)}$, aralkyl$_{(C \leq 12)}$, heteroaryl$_{(C \leq 12)}$, heteroaralkyl$_{(C \leq 12)}$, or a substituted version of these six groups;
  $R_5$ and $R_6$ are each independently hydrogen, amino, cyano, halo, hydroxy, nitro, thio, or alkyl$_{(C \leq 12)}$, cycloalkyl$_{(C \leq 12)}$, aryl$_{(C \leq 12)}$, heteroaryl$_{(C \leq 12)}$, aralkyl$_{(C \leq 12)}$, heteroaralkyl$_{(C \leq 12)}$, acyl$_{(C \leq 12)}$, alkoxy$_{(C \leq 12)}$, alkylamino$_{(C \leq 12)}$, dialkylamino$_{(C \leq 12)}$, or a substituted version of any of these ten groups, or —$(OCH_2CH_2)_xZ_1$, wherein:
    x is 0-10; and
    $Z_1$ is hydroxy, alkoxy$_{(C \leq 6)}$, or substituted alkoxy$_{(C \leq 6)}$;
  m and n are each independently 1, 2, 3, or 4;
  $X_1$ is Cl⁻, Br⁻, I⁻, PF$_6^-$, BF$_4^-$, OTf⁻, SbF$_6^-$, AgCl$_2^-$, ClO$_4^-$, NO$_3^-$, or H$_3$CC(O)O⁻.

In some embodiments, the compounds are further defined as:

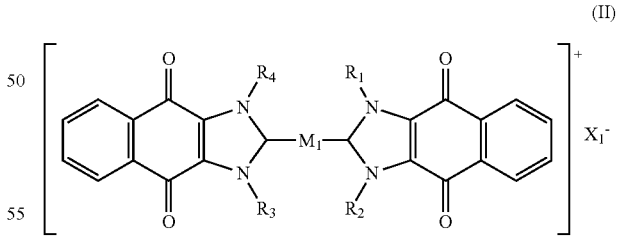

(II)

wherein:
  $M_1$ is an Au or Ag ion;
  $R_1$, $R_2$, $R_3$, and $R_4$ are each independently alkyl$_{(C \leq 12)}$, cycloalkyl$_{(C \leq 12)}$, aryl$_{(C \leq 18)}$, aralkyl$_{(C \leq 18)}$, or a substituted version of any of these groups; or —$(CR_aR_b)C(O)Y_1$; wherein:
    $Y_1$ is amino, hydroxy, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$, and $R_a$ and $R_b$ are each independently the side chain of a canonical amino acid or alkyl$_{(C≤8)}$, cycloalkyl$_{(C≤8)}$, aryl$_{(C≤12)}$, aralkyl$_{(C≤12)}$, heteroaryl$_{(C≤12)}$, heteroaralkyl$_{(C≤12)}$, or a substituted version of these six groups;

$X_1$ is Cl$^-$, Br$^-$, I$^-$, PF$_6^-$, BF$_4^-$, OTf$^-$, SbF$_6^-$, AgCl$_2^-$, ClO$_4^-$, NO$_3^-$, or H$_3$CC(O)O$^-$.

In some embodiments, $R_1$ is aryl$_{(C≤18)}$ or substituted aryl$_{(C≤18)}$. In some embodiments, $R_1$ is aryl$_{(C≤18)}$ such as phenyl, 2,6-diisopropylphenyl, or 2,4,6-trimethylphenyl. In some embodiments, $R_1$ is 2,4,6-trimethylphenyl. In some embodiments, $R_2$ is aryl$_{(C≤18)}$ or substituted aryl$_{(C≤18)}$. In some embodiments, $R_2$ is aryl$_{(C≤18)}$ such as phenyl, 2,6-diisopropylphenyl, or 2,4,6-trimethylphenyl. In some embodiments, $R_2$ is 2,4,6-trimethylphenyl.

In some embodiments, $R_3$ is aryl$_{(C≤18)}$ or substituted aryl$_{(C≤18)}$. In some embodiments, $R_3$ is aryl$_{(C≤18)}$ such as phenyl, 2,6-diisopropylphenyl, or 2,4,6-trimethylphenyl. In some embodiments, $R_3$ is 2,4,6-trimethylphenyl. In some embodiments, $R_4$ is aryl$_{(C≤18)}$ or substituted aryl$_{(C≤18)}$. In some embodiments, $R_4$ is aryl$_{(C≤18)}$ such as phenyl, 2,6-diisopropylphenyl, or 2,4,6-trimethylphenyl. In some embodiments, $R_4$ is 2,4,6-trimethylphenyl.

In some embodiments, $M_1$ is an Au ion such as a Au(I) ion. In other embodiments, $M_1$ is an Ag ion such as a Ag(I) ion. In some embodiments, $X_1^-$ is Cl$^-$. In other embodiments, $X_1^-$ is AgCl$_2^-$.

In some embodiments, $R_5$ is hydrogen, amino, cyano, halo, hydroxy, or alkyl$_{(C≤12)}$, cycloalkyl$_{(C≤12)}$, acyl$_{(C≤12)}$, alkoxy$_{(C≤12)}$, alkylamino$_{(C≤12)}$, dialkylamino$_{(C≤12)}$, or a substituted version of any of these six groups. In some embodiments, m is 1 or 2. In some embodiments, $R_6$ is hydrogen, amino, cyano, halo, hydroxy, or alkyl$_{(C≤12)}$, cycloalkyl$_{(C≤12)}$, acyl$_{(C≤12)}$, alkoxy$_{(C≤12)}$, alkylamino$_{(C≤12)}$, dialkylamino$_{(C≤12)}$, or a substituted version of any of these six groups. In some embodiments, n is 1 or 2.

In some embodiments, the compounds are further defined as:

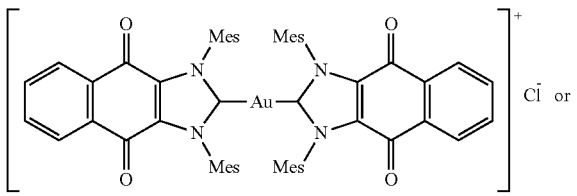

In yet another aspect, the present disclosure provides compounds of the formula:

(III)

wherein:

$M_2$ is an Au or Ag ion;

$R_7$ and $R_8$ are each independently alkyl$_{(C≤12)}$, cycloalkyl$_{(C≤12)}$, aryl$_{(C≤18)}$, aralkyl$_{(C≤18)}$, or a substituted version of any of these groups; or —(CR$_c$R$_d$)C(O)Y$_2$; wherein:

$Y_2$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$, and $R_c$ and $R_d$ are each independently the side chain of a canonical amino acid or alkyl$_{(C≤8)}$, cycloalkyl$_{(C≤8)}$, aryl$_{(C≤12)}$, aralkyl$_{(C≤12)}$, heteroaryl$_{(C≤12)}$, heteroaralkyl$_{(C≤12)}$, or a substituted version of these six groups;

$R_9$ is hydrogen, amino, cyano, halo, hydroxy, nitro, thio, or alkyl$_{(C≤12)}$, cycloalkyl$_{(C≤12)}$, aryl$_{(C≤12)}$, heteroaryl$_{(C≤12)}$, aralkyl$_{(C≤12)}$, heteroaralkyl$_{(C≤12)}$, acyl$_{(C≤12)}$, alkoxy$_{(C≤12)}$, alkylamino$_{(C≤12)}$, dialkylamino$_{(C≤12)}$, or a substituted version of any of these ten groups, or —(OCH$_2$CH$_2$)$_y$Z$_2$, wherein:

y is 0-10; and $Z_2$ is hydroxy, alkoxy$_{(C≤6)}$, or substituted alkoxy$_{(C≤6)}$;

p is 1, 2, 3, or 4; and $X_2$ is Cl$^-$, Br$^-$, I$^-$, PF$_6^-$, BF$_4^-$, OTf$^-$, SbF$_6^-$, AgCl$_2^-$, ClO$_4^-$, NO$_3^-$, or H$_3$CC(O)O$^-$.

In some embodiments, the compounds are further defined as:

(IV)

wherein:

$M_2$ is an Au or Ag ion;

$R_7$ and $R_8$ are each independently alkyl$_{(C≤12)}$, cycloalkyl$_{(C≤12)}$, aryl$_{(C≤18)}$, aralkyl$_{(C≤18)}$, or a substituted version of any of these groups; or —(CR$_c$R$_d$)C(O)Y$_2$; wherein:

$Y_2$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$, and $R_c$ and $R_d$ are each independently the side chain of a canonical amino acid or alkyl$_{(C≤8)}$, cycloalkyl$_{(C≤8)}$, aryl$_{(C≤12)}$, aralkyl$_{(C≤12)}$, heteroaryl$_{(C≤12)}$, heteroaralkyl$_{(C≤12)}$, or a substituted version of these six groups; and $X_2$ is Cl$^-$, Br$^-$, I$^-$, PF$_6^-$, BF$_4^-$, OTf$^-$, SbF$_6^-$, AgCl$_2^-$, ClO$_4^-$, NO$_3^-$, or H$_3$CC(O)O$^-$.

In some embodiments, $M_2$ is an Au ion such as Au(I). In some embodiments, $M_2$ is an Ag ion such as Ag(I). In some embodiments, $X_2$ is Cl$^-$.

In some embodiments, $R_7$ is aryl$_{(C≤18)}$ or substituted aryl$_{(C≤18)}$. In some embodiments, $R_7$ is aryl$_{(C≤18)}$ such as phenyl, 2,6-diisopropylphenyl, or 2,4,6-trimethylphenyl. In some embodiments, $R_7$ is 2,4,6-trimethylphenyl. In some embodiments, $R_8$ is aryl$_{(C≤18)}$ or substituted aryl$_{(C≤18)}$. In some embodiments, $R_8$ is aryl$_{(C≤18)}$ such as phenyl, 2,6-diisopropylphenyl, or 2,4,6-trimethylphenyl. In some embodiments, $R_8$ is 2,4,6-trimethylphenyl. In some embodiments, the compounds are not a compound of the formula:

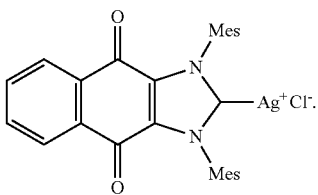

In some embodiments, the compounds are further defined as:

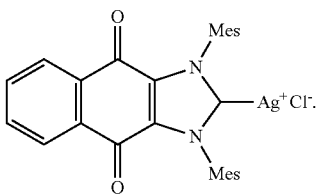

In still yet another aspect, the present disclosure provides pharmaceutical compositions comprising:

(A) a compound described herein; and (B) an excipient.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical compositions are formulated as a unit dose.

In yet another aspect, the present disclosure provides methods of treating a disease or disorder in a patient comprising administering to the patient in need thereof a therapeutically effective amount of a compound or composition described herein. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In some embodiments, the cancer is a platinum resistant cancer. In some embodiments, the platinum resistant cancer is resistant to one platinum chemotherapeutic agent. In other embodiments, the platinum resistant cancer is resistant to two or more platinum chemotherapeutic agents. In some embodiments, the platinum resistant cancer is a platinum resistant ovarian cancer, a platinum resistant lung cancer, a platinum resistant mesothelioma, a platinum resistant bladder cancer, a platinum resistant head and neck cancer, a platinum resistant cervical cancer, or a platinum resistant esophageal cancer. In some embodiments, the compound induces the cells of the cancer to undergo immunogenic cell death.

In other embodiments, the disease is an infection of a parasite. In some embodiments, the infection is of a parasite associated with a tropical disease. In some embodiments, the infection is of an intracellular parasite. In some embodiments, the treatment of the disease or disorder would benefit from the inhibition of thioredoxin reductase. In some embodiments, the treatment of the disease or disorder would benefit from the increased production of reactive oxygen species.

In some embodiments, the patient is a mammal such as a human. In some embodiments, the methods comprise administering the compound once. In other embodiments, the methods comprise administering the compound two or more times.

In still yet another aspect, the present disclosure provides methods of inducing immunological cell death in a cell comprising contacting the cell with an effective amount of a compound or composition described herein.

In yet another aspect, the present disclosure provides methods of inhibiting thioredoxin reductase comprising administering an effective amount of a compound or composition described herein.

In still another aspect, the present disclosure provides methods of increasing the production of reactive oxygen species in a cell comprising contacting the cell with an effective amount of a compound or composition described herein. In some embodiments, the methods are performed in vitro. In other embodiments, the methods are performed in vivo. In some embodiments, the cell is in a patient. In some embodiments, the thioredoxin reductase is located in a cell. In some embodiments, the cell is in a patient.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1B shows the molecular Structure of compound 3 drawn using POV-Ray. Thermal ellipsoid plots are drawn at 50% probability level and hydrogen atoms are omitted for clarity. Selected bond lengths (Å) and angles (deg): C1-N1, 1.375(10); C2-N1, 1.390(10); C1-Au1, 1.944(12); C3-O1, 1.217(6); C2-C2', 1.365(17); Au1-Cl1, 2.272(3); N1-C1-N1', 104.9(10); C1-Au1-Cl1, 177.3(4).

FIGS. 7A-7D are lateral view of 3 day old zebrafish tumor xenografts treated with 0.5 μM DMSO and FIGS. 7E-7H are lateral views of 3 day old zebrafish tumor xenografts treated with 0.5 μM Complex 1. FIG. 7A and FIG. 7E shows the DiI labeled (white arrow) A549 lung cancer cells in the DMSO and Complex 1 treated xenografts, respectively. FIG. 7B and FIG. 7F shows Acridine Orange labeled (white arrowheads) dead A549 cells within the DMSO and Complex 1 xenografts, respectively. Whereas DMSO treated xenografts display very few dead cells (FIG. 7B), complex 1 treated xenografts display cell death of majority of tumor cells (FIG. 7F). FIG. 7C and FIG. 7G are the merge of DiI and Acridine orange staining of xenografts where white spots indicate dead cells. FIG. 7D and FIG. 7H are the bright field images of DMSO and Complex 1 treated xenografts showing no non-specific cell death in the developing zebrafish larvae.

FIGS. 8A-8C show (FIG. 8A) electronic absorption spectra of compound 2 recorded in DMSO. FIG. 8B shows the electronic absorption spectra recorded during bulk reduction of compound 2 ([bis(1,3-dimesityl-4,5-naphthoquino-imidazol-2-ylidene)-gold(I) chloride) (NQ→$NQ^{2-}$) holding at −1.5 V (vs. AgCl) in DMSO with 0.1 M [N(nBu)$_4$][PF$_6$] as the supporting electrolyte at 25° C. The arrows indicate the direction of the spectral change over time. FIG. 8C shows the electronic absorption spectra recorded during bulk oxidation of reduced compound 2 ($NQ^{2-}$→NQ) holding at −0.1 V (vs. AgCl) in DMSO with 0.1 M [N(nBu)$_4$][PF$_6$] as the supporting electrolyte at 25° C. The arrows indicate the direction of the spectral change over time.

FIG. 15B shows the side by side ICP-MS detection of intracellular Au and Ag concentrations in A549 human lung cancer cells treated with 2.5 μM of complexes 1-3 for 6 h. Data illustrates similar Au uptake between 1 and 2. In addition, the Au:Ag ratio of 1 was found to be 7:1 suggesting that the $AgCl_2$ counterion does not enter the cell and possibly exchanges with other salts in cell culture medium. An Au:Ag ratio of 1:1 would suggest uptake as a complete 1*$AgCl_2$ complex. FIG. 15C shows the comparison of intracellular ROS in cells exposed to 2.5 μM either 1 or 2. FIG. 15D shows the time dependent lipoate reduction in A549 cells exposed to 0.6125 μM of either 1 or 2. FIG. 15E shows the normalized lipoate reduction in A549 cells exposed to 1 or 2 across multiple concentrations. Error bars represent SEM.

DESCRIPTION OF ILLUSTRATIVE EMBODIMENTS

Figure 1A:
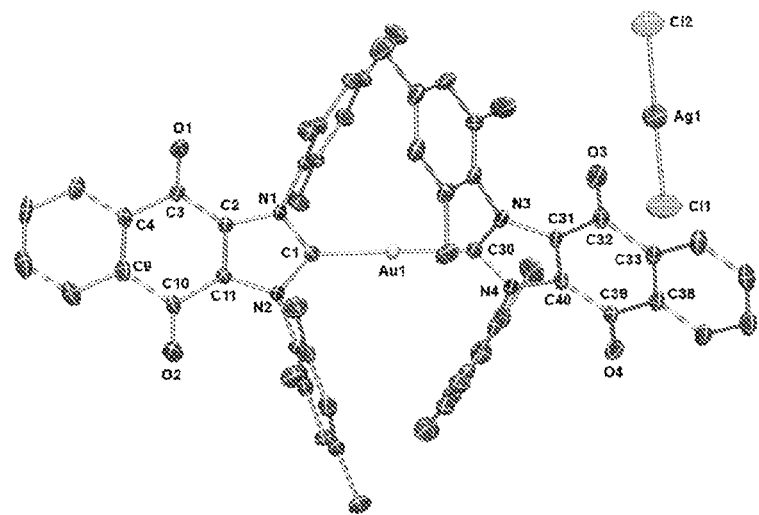
FIGS. 1A & 1B shows (FIG. 1A) the ORTEP plot of Compound 1 drawn using POV-Ray. Thermal ellipsoid plots are drawn at the 50% probability level and hydrogen atoms are omitted for clarity. Selected bond lengths (Å) and angles (deg): C1-N1, 1.347(6); C1-N2, 1.359(6); C30-N3, 1.356(6); C30-N4, 1.360(6); C1-Au1, 2.012(5); C30-Au1, 2.009(5); C3-O1, 1.217(6); C10-O2, 1.219(6); C39-O4, 1.207(6); C32-O3, 1.221(6); C11-C2, 1.350(7); C40-C31, 1.365(7); Cl1-Ag1, 2.3210(19); Cl2-Ag1, 2.3325(17); N1-C1-N2, 106.4(4); N3-C30-N4, 105.9(4); C1-Au1-C30, 172.87(19); Cl1-Ag1-Cl2, 178.46(8).

In some aspects, the present disclosure provides gold carbene naphthoquinone compounds which contain two different therapeutically active centers. Without wishing to be bound by any theory, it is believed that the naphthoquinone complex may act as a redox cycling agent, which results in an increase reactive oxygen species production, while the gold carbene portion of the molecule acts as thioredoxin reductase inhibitor thus reducing the cell's ability to modulate the effects of the reactive oxygen species. These compounds may be used in the treatment of cancers including platinum resistant cancers or in a parasitic infection. These compounds and related compositions and methods are described in more detail below.

A. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2H$); "halo" means independently —F, —Cl, —Br or —I; "amino" means —$NH_2$; "hydroxyamino" means —NHOH; "nitro" means —$NO_2$; imino means =NH; "cyano" means —CN; "isocyanate" means —N=C=O; "azido" means —$N_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol " ---- " represents an optional bond, which if present is either single or double. The symbol " ==== " represents a single bond or a double bond. Thus, for example, the formula

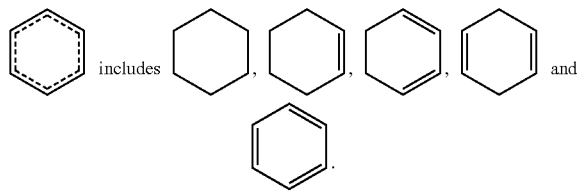

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ⌇ ", when drawn perpendicularly across a bond

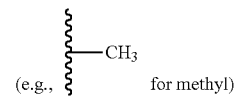

indicates a point of attachment of the group. It is noted that the point of attachment is typically only identified in this manner for larger groups in order to assist the reader in unambiguously identifying a point of attachment. The symbol " ◄■ " means a single bond where the group attached to the thick end of the wedge is "out of the page." The symbol " ιιιιιι " means a single bond where the group attached to the thick end of the wedge is "into the page". The symbol " ⌇ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

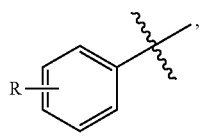

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

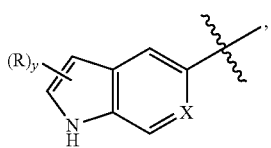

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, a linear or branched cyclo or cyclic structure, no carbon-carbon double or triple bonds, and no atoms other than carbon and hydrogen. As used herein, the cycloalkyl group may contain one or more branching alkyl groups (carbon number limit permitting) attached to the ring system so long as the point of attachment is the ring system. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, a linear or branched cyclo or cyclic structure, no carbon-carbon double or triple bonds, and no atoms other than carbon and hydrogen.

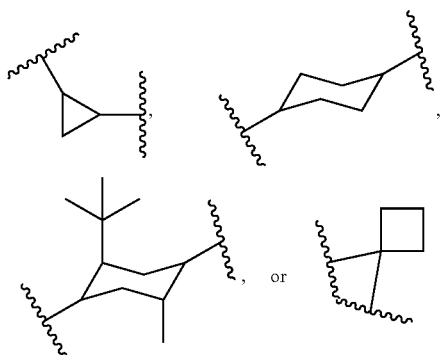

are non-limiting examples of cycloalkanediyl groups. The term "cycloalkylidene" when used without the "substituted" modifier refers to the divalent group =CRR' in which R and R' are taken together to form a cycloalkanediyl group with at least two carbons. Non-limiting examples of alkylidene groups include: =C(CH$_2$)$_2$ and =C(CH$_2$)$_5$. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

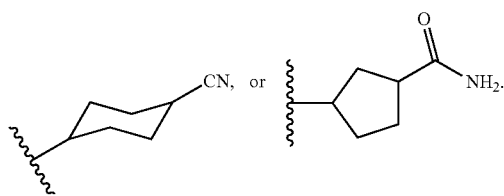 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

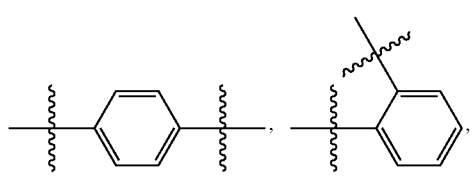

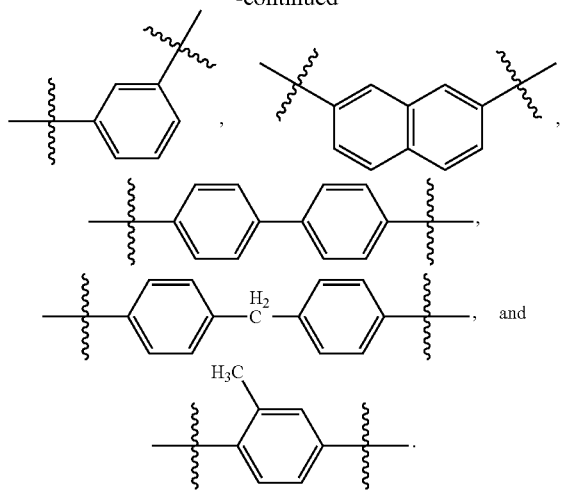

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group alkanediylaryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

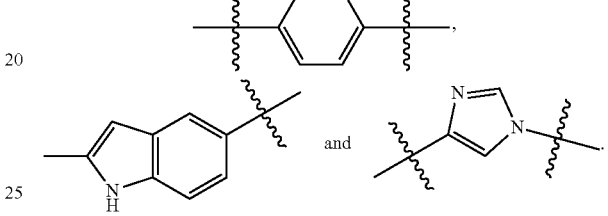

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "cycloalkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, cycloalkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The terms "alkylthio", "cycloalkylthio", and "acylthio" when used without the "substituted" modifier refers to the group —SR, in which R is an alkyl, cycloalkyl, and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. The term "dicycloalkylamino" or "diarylamino" when used without the "substituted" modifier refers to the group —NRR', in which R and R' can each independently be the same or different cycloalkyl or aryl groups, respectively. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "acylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an acylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "platinum chemotherapeutic agent" is an organic compound which contains platinum as an integral part of the molecule. Examples of platinum-based chemotherapeutic agents include carboplatin, cisplatin, and oxaliplatin.

A "platinum resistant" cancer is a cancer in a patient has progressed while receiving platinum chemotherapeutic agent (i.e. the patient is "platinum refractory"), or the patient has progressed within 12 months (for instance, within 6 months) after completing a course of platinum chemotherapeutic agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

In the context of this application, "selectively" means that greater than 50% of the activity of the compound is exhibited in the noted location. On the other hand, "preferentially" means that greater than 75% of the activity of the compound is exhibited in the noted location.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that for tetrahedral stereogenic centers the stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

B. Compounds of the Present Disclosure

In some aspects, the present disclosure relates to compounds of the formula:

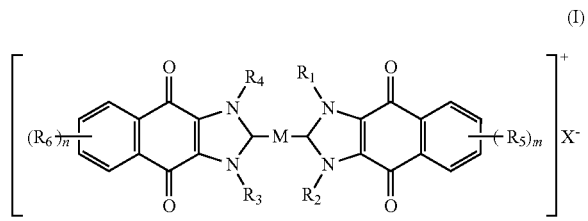

wherein:

M is an Au or Ag ion;

$R_1$, $R_2$, $R_3$, and $R_4$ are each independently alkyl$_{(C≤12)}$, cycloalkyl$_{(C≤12)}$, aryl$_{(C≤18)}$, aralkyl$_{(C≤18)}$, or a substituted version of any of these groups; or —(CR$_a$R$_b$)C(O)Y$_1$; wherein:

$Y_1$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$; and $R_a$ and $R_b$ are each independently the side chain of a canonical amino acid or alkyl$_{(C≤8)}$, cycloalkyl$_{(C≤8)}$, aryl$_{(C≤12)}$, aralkyl$_{(C≤12)}$, heteroaryl$_{(C≤12)}$, heteroaralkyl$_{(C≤12)}$, or a substituted version of these six groups;

$R_1$ and $R_6$ are each independently hydrogen, amino, cyano, halo, hydroxy, nitro, thio, or alkyl$_{(C≤12)}$, cycloalkyl$_{(C≤12)}$, aryl$_{(C≤12)}$, heteroaryl$_{(C≤12)}$, aralkyl$_{(C≤12)}$, heteroaralkyl$_{(C≤12)}$, acyl$_{(C≤12)}$, alkoxy$_{(C≤12)}$, alkylamino$_{(C≤12)}$, dialkylamino$_{(C≤12)}$, or a substituted version of any of these ten groups;

m and n are each independently 1, 2, 3, or 4;

X is Cl$^-$, Br$^-$, I$^-$, PF$_6^-$, BF$_4^-$, OTf$^-$, SbF$_6^-$, AgCl$_2^-$, ClO$_4^-$, NO$_3^-$, or H$_3$CC(O)O$^-$.

In other aspects, the present disclosure provides compounds of the formula:

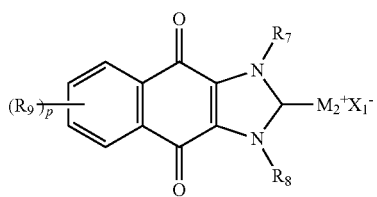

(III)

wherein:
M$_2$ is an Au or Ag ion;
R$_7$ and R$_8$ are each independently alkyl$_{(C≤12)}$, cycloalkyl$_{(C≤12)}$, aryl$_{(C≤18)}$, aralkyl$_{(C≤18)}$, or a substituted version of any of these groups; or —(CR$_c$R$_d$)C(O)Y$_2$;
wherein:
Y$_2$ is amino, hydroxy, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, or substituted dialkylamino$_{(C≤8)}$, and
R$_c$ and R$_d$ are each independently the side chain of a canonical amino acid or alkyl$_{(C≤8)}$, cycloalkyl$_{(C≤8)}$, aryl$_{(C≤12)}$, aralkyl$_{(C≤12)}$, heteroaryl$_{(C≤12)}$, heteroaralkyl$_{(C≤12)}$, or a substituted version of these six groups;
R$_9$ is hydrogen, amino, cyano, halo, hydroxy, nitro, thio, or alkyl$_{(C≤12)}$, cycloalkyl$_{(C≤12)}$, aryl$_{(C≤12)}$, heteroaryl$_{(C≤12)}$, aralkyl$_{(C≤12)}$, heteroaralkyl$_{(C≤12)}$, acyl$_{(C≤12)}$, alkoxy$_{(C≤12)}$, alkylamino$_{(C≤12)}$, dialkylamino$_{(C≤12)}$, or a substituted version of any of these ten groups;
p is 1, 2, 3, or 4; and
X$_2$ is Cl$^-$, Br$^-$, I$^-$, PF$_6^-$, BF$_4^-$, OTf$^-$, SbF$_6^-$, AgCl$_2^-$, ClO$_4^-$, NO$_3^-$, or H$_3$CC(O)O$^-$.

The compounds provided by the present disclosure are shown, for example, above in the summary section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. In the context of this disclosure, metal complexes may exist in each of their isomeric forms such that the ligands may be rearranged to form the other isomers. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. Additionally, stereoisomers of the metal center including the Ag or Au cation arising from the various arrangements of the ligands around the metal ion are also contemplated.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Additionally, the metal ions in the present disclosure can have different oxidation states unless otherwise noted. As used herein, the charge on the metal atom can be denoted either as a superscript such as Au$^I$ or using parenthesis such as Au(I). These two forms are identical as would be recognized to a person of skill in the art. Even if one form is used in the application to describe the oxidation state in one place in the application, it is contemplated that the other form could be used in elsewhere in the application.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds provided herein are within the scope of the disclosure. It will also be appreciated by those skilled in organic chemistry that many organic compounds can exist in more than one crystalline form. For example, crystalline form may vary from solvate to solvate. Thus, all crystalline forms of the compounds provided herein or the pharmaceutically acceptable solvates thereof are within the scope of the present disclosure.

C. Diseases and Disorders I. Hyperproliferative Diseases While hyperproliferative diseases can be associated with any medical disorder that causes a cell to begin to reproduce uncontrollably, the prototypical example is cancer. One of the key elements of cancer is that the normal apoptotic cycle of the cell is interrupted and thus agents that lead to apoptosis of the cell are important therapeutic agents for treating these diseases. As such, the gold carbene naphthoquinone compounds and compositions described in this disclosure may be effective in treating cancers.

Cancer cells that may be treated with the compounds according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

II. Parasitic Infections

Parasite presents a major health issue, particularly in under-developed countries around the world. Significant pathogenic parasites include *Entamoeba histolytica, Giardia lamblia, Trichomonas vaginalis, Plasmodium falciparum, Plasmodium malariae, Plasmodium ovale, Plasmodium vivax, Plasmodium knowlesi, Rhinosporidium seeberi, Trypanosoma brucei, Trypanosoma vaginalis, Naegleria fowleri, Isospora belb, Dientamoeba fragilis, Cyclospora cayetanensis, Cryptosporidium* spp., *Balantidium coli, Babesia divergens, Babesia bigeminia, Babesia equi, Babesia microffti, Babesia duncani, Balamuthia mandrillaris, Blastocystis* spp., *Acanthamoeba* spp., *Trypanosoma gambiense, Trypanosoma rhodesiense, Trypanosoma cruzi, Ascaris lumbricoides, Trichinella spiralis, Toxoplasma gondii, Leishmania donovani, Leishmania tropica, Leishmania braziliensis, Schistosoma mansoni, Schistosoma japonicum, Schistosoma haematobium,* and *Pneumocystis jiroveci.* The compounds and compositions of the present disclosure may be used in the treatment of these pathogenic parasites. Additionally, in some embodiments, these compounds and compositions may be used in the treatment of helminths (worms) such as tapeworms, flukes, and roundworms.

D. Pharmaceutical Formulations and Routes of Administration

For administration to a mammal in need of such treatment, the gold carbene naphthoquinone compounds and compositions of the present disclosure are ordinarily combined with one or more excipients appropriate to the indicated route of administration. The gold carbene naphthoquinone compounds and compositions of the present disclosure may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present disclosure may be subjected to conventional pharmaceutical operations such as sterilization and/or may contain conventional pharmaceutical carriers and excipients such as preservatives, stabilizers, wetting agents, emulsifiers, buffers, etc.

The gold carbene naphthoquinone compounds and compositions of the present disclosure may be administered by a variety of methods, e.g., orally or by injection (e.g. subcutaneous, intravenous, intraperitoneal, etc.). Depending on the route of administration, the novel compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the gold carbene naphthoquinone compounds and compositions of the present disclosure with, or co-administer the gold carbene naphthoquinone compounds and compositions of the present disclosure with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes. Additionally, Trapasol®, Travasol®, cyclodextrin, and other drug carrier molecules may also be used in combination with the gold carbene naphthoquinone compounds and compositions of the present disclosure.

The gold carbene naphthoquinone compounds and compositions of the present disclosure may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion are also envisioned. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the gold carbene naphthoquinone compounds and compositions of the present disclosure in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The gold carbene naphthoquinone compounds and compositions of the present disclosure can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the gold carbene naphthoquinone compounds and compositions of the present disclosure in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of the gold carbene naphthoquinone compounds and compositions of the present disclosure calculated to produce the desired therapeutic effect in association with the required pharmaceutical carrier. The specification for the dosage unit forms of the disclosure are dictated by and directly dependent on (a) the unique characteristics of the gold carbene naphthoquinone compounds and compositions of the present disclosure and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The gold carbene naphthoquinone compounds and compositions of the present disclosure describe in this disclosure are administered at a therapeutically effective dosage sufficient to treat a condition associated with a condition in a patient. For example, the efficacy of the gold carbene naphthoquinone compounds and compositions of the present disclosure can be evaluated in an animal model system that may be predictive of efficacy in treating the disease in humans, such as the model systems shown in the examples and drawings.

The actual dosage amount of the gold carbene naphthoquinone compounds and compositions of the present disclosure or composition comprising the compounds of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 1 mg/kg to about 50 mg/kg, in one or more dose administrations daily, for one or several days (depending of course of the mode of administration and the factors discussed above). In some particular embodiments, the amount is less than 5,000 mg per day with a range of 10 mg to 4500 mg per day.

The effective amount may be less than 10 mg/kg/day, less than 50 mg/kg/day, less than 100 mg/kg/day, less than 250 mg/kg/day. It may alternatively be in the range of 1 mg/kg/day to 250 mg/kg/day.

In other non-limiting examples, a dose may also comprise from about 0.1 mg/kg/body weight, about 1 mg/kg/body weight, about 10 g/kg/body weight, about 50 g/kg/body weight, or more per administration, and any range derivable therein. In non-limiting examples of a derivable range from the numbers listed herein, a range of about 1 mg/kg/body weight to about 50 mg/kg/body weight, about 5 g/kg/body weight to about 10 g/kg/body weight, etc., can be administered, based on the numbers described above.

In certain embodiments, a pharmaceutical composition of the present disclosure may comprise, for example, at least about 0.1% of a compound described in the present disclosure. In other embodiments, the compound of the present disclosure may comprise between about 0.25% to about 75% of the weight of the unit, or between about 25% to about 60%, or between about 1% to about 10%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agents are administered once a day.

The compounds may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may taken orally and that the timing of which is or is not dependent upon food intake. Thus, for example, the agents can be taken every morning and/or every evening, regardless of when the subject has eaten or will eat.

E. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods for the Preparation and Use of Naphtho-quinone Fused Gold(I) N-Heterocyclic Carbene Complexes A. Synthesis and Characterization Complex 1 ([(4)$_2$Au][AgCl$_2$]) was prepared in 82% yield by treating 1 equiv of (4)Ag—Cl (Sanderson et al., 2006; Tennyson et al., 2010) with 0.45 equiv of (C$_4$H$_8$S)Au—Cl (Scheme 1) (Wang and Lin, 1998). Proton NMR spectral analyses of 1 in CD$_2$Cl$_2$ proved consistent with the molecular structure of [(4)$_2$Au]$^+$. For instance, mesityl-CH$_3$ hydrogen signals (ortho-CH$_3$), corresponding to 24 hydrogen atoms, were observed at 1.63 ppm, while mesityl-CH$_3$ hydrogen signals (para-CH$_3$), corresponding to 12 hydrogen atoms, were observed at 2.43 ppm. A significant upfield shift (1.63 ppm) in the mesityl-CH$_3$ hydrogen signals (ortho-CH$_3$) was seen, and was taken as evidence for the presence of a [(4)$_2$Au]$^+$ subunit, as observed for other reported [bis(NHC)Au]$^+$ complexes (wherein the corresponding signal resonates at 1.68 ppm in CDCl$_3$) (Santoro et al., 2015). In the $^{13}$C NMR spectrum (CD$_2$Cl$_2$), a diagnostic chemical shift corresponding to C$_{carbene}$—Au—C$_{carbene}$ for 1 was observed at δ $^{13}$C (Au—C$_{carbene}$)=192.6 ppm. This corresponds to a downfield shift compared to other reported [(NHC)—Au—(NHC)]$^+$ complexes, such as bis(1-(ferrocenylmethyl)-3-mesitylimidazol-2-ylidene)-gold(I) (δ $^{13}$C (Au—C$_{carbene}$)=183.2 ppm, CDCl$_3$), (Arambula et al., 2016) bis(1,3-dimesitylimidazol-2-ylidene)-gold(I) tetrafluoroborate (δ $^{13}$C (Au—C$_{carbene}$)=185.1 ppm, CDCl$_3$), (Santoro et al., 2015) bis(1,3-dimethylimidazol-2-ylidene)-gold(I) bromide (δ $^{13}$C (Au—C$_{carbene}$)=183.3 ppm, (CD$_3$)$_2$SO) (Baker et al., 2006), and bis(1,3-dicyclohexylimidazol-2-ylidene)-gold(I) chloride (δ $^{13}$C (Au—C$_{carbene}$)=180.4 ppm, (CD$_3$)$_2$SO) (Baker et al., 2006) and is ascribed to the presence of the fused electron-withdrawing quinone that supports π-backbonding (Sanderson et al., 2006).

[Bis(1,3-dimesityl-4,5-naphthoquino-imidazol-2-ylidene)-gold(I)] [Silver(I) dichloride], Compound 1. (1,3-Dimesitylnaphthoquinimidazol-2-ylidene)-silver chloride (117.4 mg, 0.203 mmol, 1.0 eq) and (C$_4$H$_8$S)AuCl (29.3 mg, 0.0914 mmol, 0.45 eq) were combined in a 20 mL scintillation vial with 4 mL THF under an inert atmosphere. After stirring at 60° C. for 16 h, the mixture was decanted, and the dark solid was washed with 3×5 mL of Et$_2$O to reveal a yellow product. This was dissolved in minimal CH$_2$Cl$_2$ and filtered through a plug of Celite® into a pre-weighed 20 mL scintillation vial; the solvent was removed under reduced pressure. Yield: 82.1%. $^1$H NMR (δ, CD$_2$Cl$_2$, 300 MHz):

1.63 (s, 24H, Mes), 2.43 (s, 12H, Mes), 6.97 (s 8H, Mes), 7.71-7.77 (m, 4H, NQ), 7.95-8.00 (m, 4H, NQ). $^{13}$C NMR ($\delta$, CD$_2$Cl$_2$, 75 MHz): 17.6, 21.6, 127.7, 129.9, 132.3, 132.5, 132.7, 134.4, 135.6, 141.0, 174.4, 192.6. HRMS (ESI) for [C$_{58}$H$_{52}$N$_4$O$_4$Au]$^+$ [M]$^+$ Calcd. 1065.3654 Found 1065.3656. Anal. Calcd. for: C$_{58}$H$_{52}$N$_4$O$_4$AuAgCl$_2$: C, 55.96; H, 4.21; N, 4.50. Found: C, 56.48; H, 4.34; N, 4.56. IR (cm$^{-1}$): 1681 (KBr).

An analogue of 1 ([(4)$_2$Au][AgCl$_2$]) containing a [Cl]$^-$ counterion (complex 2) was also prepared. Complex 2 was synthesized in 75% yield by treating the free carbene 4 (1,3-dimesitylnaphthoquinimidazol-2-ylidene), generated in situ, with 0.45 equiv. of (C$_4$H$_8$S)Au—Cl (Scheme 1). As true for 1, $^1$H NMR spectral analyses of 2 in CD$_2$Cl$_2$ proved consistent with the presence of the [(4)$_2$Au]$^+$ cation core. Using a modified literature procedure, a charge neutral mono-NHC functionalized gold(I) NHC (with NHC=1-benzyl-3-mesityl-imidazol-2-ylidene) complex analogous to 1 (3) was also prepared (Perez-Galan et al., 2016). It was obtained in 68% yield by treating 1 equiv of (4)Ag—Cl with 1 equiv of (C$_4$H$_8$S)Au—Cl. $^1$H NMR spectral analysis (CD$_2$Cl$_2$) of 3 was consistent with the proposed structure, whereas the $^{13}$C NMR (CD$_2$Cl$_2$) spectrum revealed that the diagnostic $\delta$ Au—C$_{carbene}$ resonance appeared at 183.4 ppm. Again, this value is shifted downfield relative to other reported (NHC)Au—Cl complexes, for which corresponding resonances at ca. 168 ppm are seen (de Fremont et al., 2005). Gold complexes 1-3 were also characterized by ultraviolet-visible spectroscopy and infrared spectroscopy.

[Bis(1,3-dimesityl-4,5-naphthoquino-imidazol-2-ylidene)-gold(I) Chloride, Compound 2. 1,3-Dimesitylnaphthoquinimidazolium chloride (85.2 mg, 0.1809 mmol, 1.0 eq) was added to NaHMDS (33.2 mg, 0.1809 mmol, 1.0 eq) in a 20 mL scintillation vial and stirred at 25° C. for 16 h in 2 mL of toluene. The resulting mixture was filtered through a plug of Celite® into a pre-weighed 20 mL scintillation vial containing (C$_4$H$_8$S)AuCl (26.1 mg, 0.081 mmol, 0.45 eq) and stirred at 25° C. for thirty minutes. The dark precipitate was subjected to a series of washes (2×4 mL of toluene and then 3×4 mL of Et$_2$O) to yield a yellow solid (67.0 mg). Yield: 74.7%. $^1$H NMR ($\delta$, CD$_2$Cl$_2$, 300 MHz): 1.74 (s, 24H, Mes), 2.55 (s, 12H, Mes), 7.08 (s 8H, Mes), 7.83-7.89 (m, 4H, NQ), 8.06-8.12 (m, 4H, NQ). $^{13}$C NMR ($\delta$, CD$_2$Cl$_2$, 75 MHz): 17.6, 21.6, 127.7, 129.9, 132.2, 132.5, 132.7, 134.4, 135.6, 141.0, 174.4, 192.6. HRMS (ESI) for [C$_{58}$H$_{52}$N$_4$O$_4$Au] [M]$^+$ Calcd. 1065.3654 Found 1065.3665. Anal. Calcd. for: C$_{58}$H$_{52}$N$_4$O$_4$AuCl: C, 63.24; H, 4.76; N, 5.09. Found: C, 63.33; H, 4.73; N, 5.05. IR (cm$^{-1}$): 1681 (KBr).

(1,3-Dimesityl-4,5-naphthoquino-imidazol-2-ylidene)-gold(I) Chloride, Compound 3. (1,3-Dimesitylnaphthoquinimidazol-2-ylidene)-silver chloride (119.4 mg, 0.206 mmol, 1.0 eq) and (C$_4$H$_8$S)AuCl (66.1 mg, 0.206 mmol, 1 eq) were combined in a 20 mL scintillation vial with 4 mL THF under an inert atmosphere. After stirring at 40° C. for 5 h, the opaque reaction mixture was stirred for an additional 12 h at 25° C. This was then filtered through a plug of Celite® into a pre-weighed 20 mL scintillation vial, and the solvent was removed under reduced pressure. The resulting solid was washed successfully with 3×5 mL of Et$_2$O to reveal a yellow product. Yield: 67.8%. $^1$H NMR ($\delta$, CD$_2$Cl$_2$, 300 MHz): 2.15 (s, 12H, Mes), 2.49 (s, 6H, Mes), 7.20 (s 4H, Mes), 7.83-7.89 (m, 4H, NQ), 8.11-8.16 (m, 4H, NQ). $^{13}$C NMR ($\delta$, CD$_2$Cl$_2$, 75 MHz): 18.2, 21.5, 127.5, 130.0, 132.3, 132.4, 133.4, 134.6, 135.3, 141.1, 174.6, 183.4. HRMS (ESI) for [C$_{29}$H$_{26}$N$_2$O$_2$AuCl] [M+Na]$^+$ Calcd. 689.1246. Found 689.1230. Anal. Calcd. for: C$_{29}$H$_{26}$N$_2$O$_2$AuCl: C, 52.23; H, 3.93; N, 4.20. Found: C, 51.98; H, 3.85; N, 4.12. IR (cm$^{-1}$): 1679 (KBr).

Figure 1B:
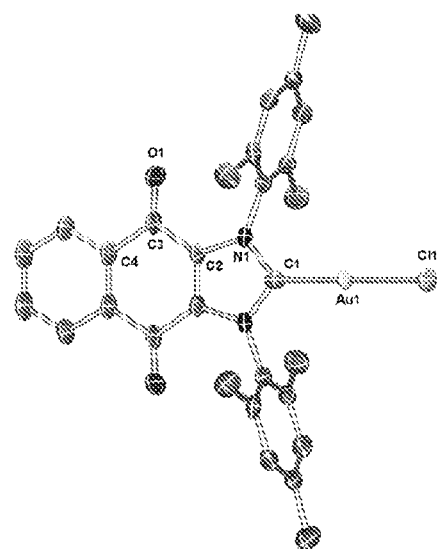

To assign the molecular structure unambiguously, X-ray diffraction quality single crystals of 1 and 3 were grown by slowly diffusing hexanes into a concentrated 1,2-dichloroethane solution. Thermal ellipsoid plot of the resulting structure is presented in FIGS. 1A & 1B. In the case of 1, a trans geometry was seen for the core [(4)$_2$Au]$^+$ cation with a C—Au—C bond angle of 172.8(2)° being observed. The Au—C$_{carbene}$ bond distances of 2.012(5) Å and 2.009(4) Å are in agreement with those for other reported NHC—Au—NHC complexes (Baker et al., 2004; Kalyanaraman et al., 2004; Santoro et al., 2015; de Fremont et al., 2005; Hu et al., 2004). As inferred from the molecular structure of 1, (FIG. 1A), the two carbene units are rotated around the gold atom with a torsion angle of 62.6(3)°. Without wishing to be bound by any theory, it is believed that this twisting minimizes steric crowding.

TABLE S1

Crystallographic and refinement data.

| | Compound 1 | Compound 3 |
|---|---|---|
| CCDC | 1520307 | 1537344 |
| solvent | none | used squeeze |
| formula | C$_{58}$H$_{52}$N$_4$O$_4$AuAgCl$_2$ | C$_{29}$H$_{26}$AuClN$_2$O$_2$ |
| fw | 1244.7 | 666.95 |
| xtl system | orthorhombic | tetragonal |
| space grp | Pna2(1) | I-42m |
| color, habit | yellow, rod | Yellow, block |
| a, Å | 22.040 (3) | 19.1131 (19) |
| b, Å | 16.674 (2) | 19.1131 (19) |
| c, Å | 14.244 (2) | 14.8158 (16) |
| $\alpha$, deg. | 90.00 | 90.00 |
| $\beta$, deg. | 90.00 | 90.00 |
| $\gamma$, deg. | 90.00 | 90.00 |
| V, Å$^3$ | 5234.7 (11) | 5412.37 |
| T, K | 150 (2) | 171K |
| Z | 4 | 8 |
| R1, wR2$^a$ | 0.023, 0.064 | 0.0292, 0.0618 |
| GoF on F$^2$ | 1.049 | 1.072 |

$^a$R1 = $\Sigma||F_o| - |F_c||/\Sigma|F_o|$.
$^b$ R$_w$ ={[$\Sigma$w(F$_o^2$ − F$_c^2$)$^2$/$\Sigma$w(F$_o^2$)$^2$]$^{1/2}$; w = 1/[$\sigma^2$(F$_o^2$) + (xP)$^2$], where P = (F$_o^2$ + 2F$_c^2$)/3.

B. Electrochemistry

A series of electrochemical analyses, including cyclic voltammetry (CV) and differential pulse voltammetry (DPV), were carried out with [NnBu$_4$][PF$_6$] in anhydrous dimethyl sulfoxide (DMSO) in order to evaluate electronic properties of compounds 1-3 and 4[H][Cl]. Key half-wave reduction potentials for 1-3 and 4[H][Cl], obtained from DPV measurements, are summarized in Table 1. In the CV measurements (scan rate=100 mV s$^{-1}$), all four compounds (1-3 and 4[H][Cl]) displayed cathodic waves that occur in two sequential steps in which the first wave is completely reversible and the second wave is quasireversible at a 0.1 mV/s scan rate; these are labeled as a and b in Table 1 (Guth et al., 2011; Gómez et al., 2003). These electrochemical features were attributed to the reduction of the quinone moiety to first produce the semiquinone radical (NQ$^-$) and then produce the quinone dianion (NQ$^{2-}$) forms of compounds 1-3 and 4[H] [Cl] (Guth et al., 2011; Gómez et al., 2003). The quinone reduction potential in 4[H][Cl] occurs at −0.38 V, the lowest of all the molecules studied, indicative of a positively charged imidazolium ring. The quinone couple at −0.42 V observed for compound 1 is ascribed to the presence of bis(NHC). The same wave in compound 3 appears at a more negative potential (−0.47 V), presumably due to greater trans effects excreted by quinone annulated NHC ligand than the metal-bound chloride. This analysis agrees well with the differences in the observed δ $^{13}$C (Au—C$_{carbene}$) resonances for compounds 1 and 3.

TABLE 1

Electrochemical analysis of compounds 1-3 and 4[H][Cl].

| Compound | E$_{1/2}$ (V) DPV | E$_{1/2}$[b] (V) DPV |
|---|---|---|
| Compound 1 | −0.42 | −1.31 |
| Compound 2 | −0.46 | −1.31 |
| Compound 3 | −0.47 | −1.31 |
| Compound 4[H][Cl] | −0.38 | −1.15 |

The potentials were obtained from cyclic voltammetry and differential pulse voltammetry measurements in DMSO using 0.1M [N(nBu)$_4$]$^+$[PF$_6$]$^−$ as the supporting electrolyte, 0.1 mM analyte, and referenced vs SCE.
Assigned as the first reduction, formation of semiquinone radical (NQ$^{•−}$),[b] assigned as the second reduction, formation of quinone dianion (NQ$^{2−}$).

Figure 8A:
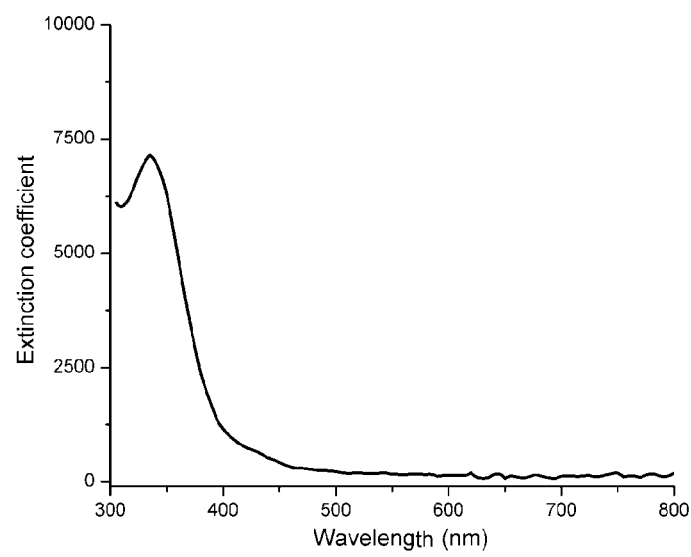
Figure 8B:
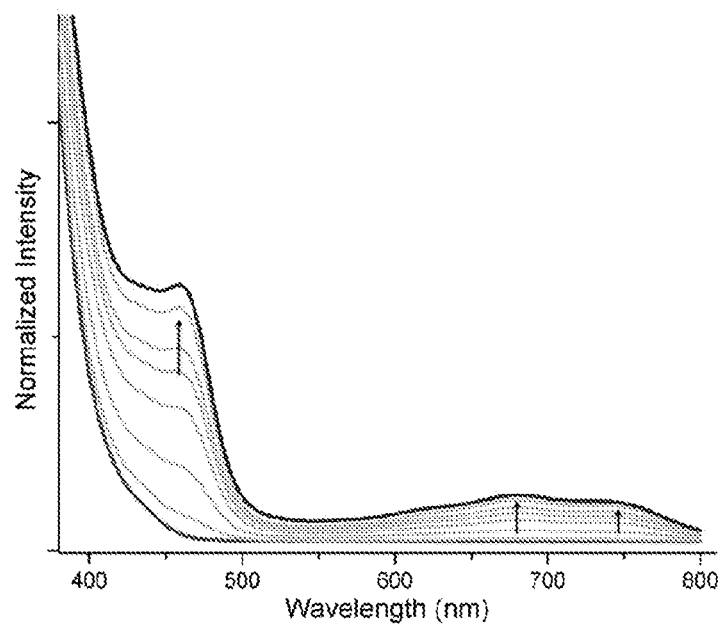
FIG. 8B shows dose responsive inhibition of TrxR activity in A549 cells treated with 0.156-5.0 μM compound for 6 hr and then incubated for 3 hr with lipoate. Doxorubicin data are not shown for clarity.
Figure 8C:
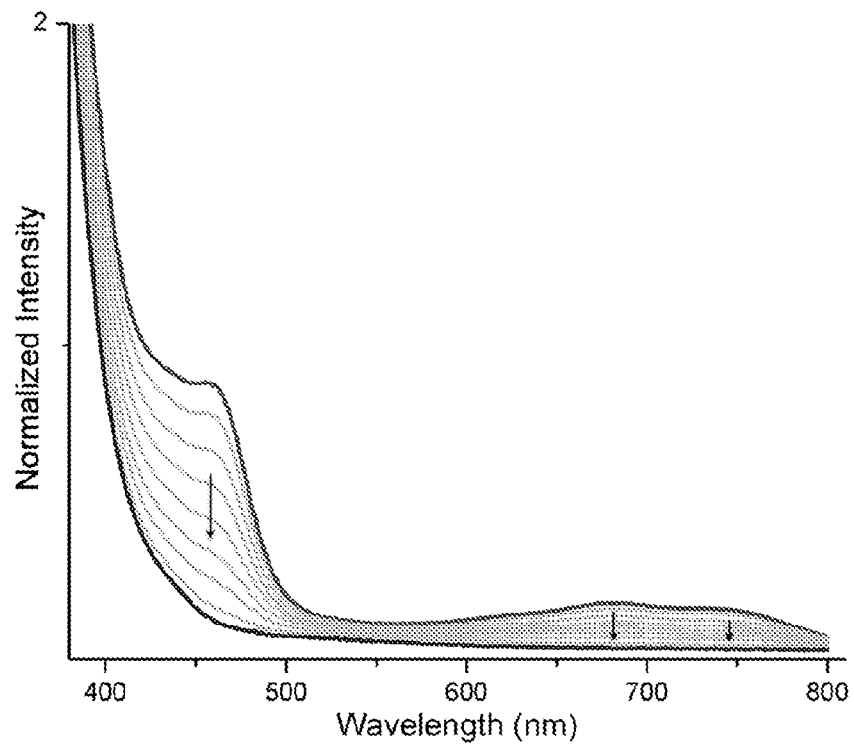

Having studied the electronic properties, the stability and electronic nature of 1 upon reduction by means of UV-vis spectroelectrochemistry was probed. Upon bulk electrolysis of compound 2 at a potential of −1.5 V using a special electrochemical cell, reduced quinone species were generated and simultaneously probed using UV-vis spectroscopy. Characteristic absorbance features ascribable to reduced quinone moieties were observed (Tennyson et al., 2010). The original UV-Vis spectral trace of compound 2 can be obtained after reduction (NQ→NQ$^{2−}$) followed by subsequent oxidation (NQ$^{2−}$→NQ) (see FIG. 8A-8C). These findings provide support for the reduced species being stable under the conditions of electrochemical analysis.

C. Cell Proliferation Assays

Figure 2:
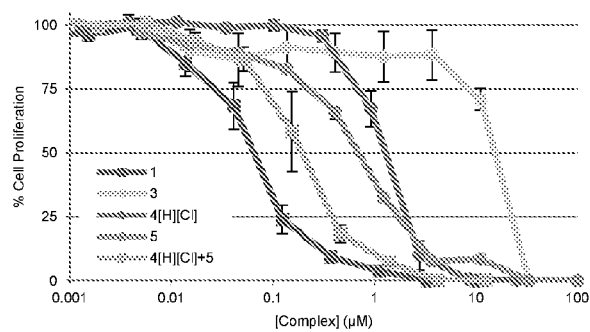
FIG. 2 shows cell proliferation profiles of A549 lung cancer cells treated with 1, 3, 4[H] [Cl], 5, and a 2:1 molar concentration of 4[H] [Cl] and 5 (cocktail), respectively. Data for doxorubicin and auranofin are not shown for clarity purposes but are provided in Table 2. Error bars represent the standard error of the mean.
Figure 9:
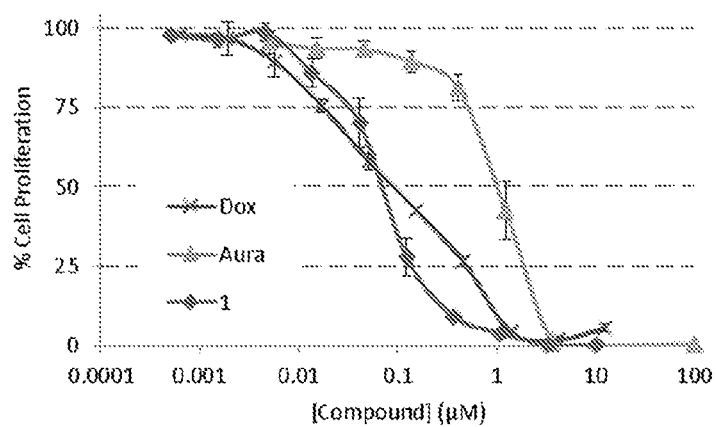
FIG. 9 shows the cell proliferation profile of A549 lung cancer cells treated with 1, doxorubicin, and auranofin for 72 h. Error bars represent SEM.

To gauge the ability of each complex to inhibit cancer cell growth, A549 lung cancer cells were treated with 1-3, 4[H][Cl], doxorubicin, and auranofin in a dose responsive manner. Cellular vitality, specifically mitochondrial reductase activity, was then quantified colorimetrically post treatment using 3-(4,5-dimethylthiazol-2-yl)-2,5-diphenyltetrazolium bromide (MTT assay) (Table 2, FIG. 2). Dose responsive treatment of A549 cells with doxorubicin and auranofin provided growth inhibition curves and IC$_{50}$ values of 0.103±0.023 μM and 1.67±0.05 μM, respectively (FIG. 9). These values were similar to those previously reported (Arambula et al., 2016; Poornima et al., 2014). In the case of the gold(I) NHC quinone complex 1, the corresponding IC$_{50}$ value was determined to be 0.073±0.016 μM. A similar value was recorded in the case of complex 2. Complex 3 was essentially inactive (i.e., >150× less potent than 1).

TABLE 2

Cell proliferation data in A549 lung cancer cells.

| Compound | IC$_{50}$ (μM) | Std Error (+/−) | Fold Difference relative to 1 |
|---|---|---|---|
| Doxorubicin | 0.103 | 0.023 | 1.41 |
| Auranofin | 1.67 | 0.05 | 22.9 |
| 1[a] | 0.073 | 0.016 | 1 |
| 2 | 0.075 | 0.013 | 1 |
| 3 | 12.06 | 0.18 | 165 |
| 4 | 0.994 | 0.12 | 13.6 |
| 5 | 0.71 | 0.06 | 9.72 |
| 4[H][Cl] + 5[b] | 0.197 | 0.057 | 2.70 |

[a]Students t-test (unpaired) provided a p-value <0.05 when 1 was compared to 3, 4[H][Cl], 5, and cocktail (4[H][Cl] + 5).
[b]Cocktail dosing entailed a 2:1 molar ratio of 4[H][Cl] and 5, respectively. This dosing reflects the relative component stoichiometry in complex 1.

To determine the relative contribution of the individual components present in 1 (i.e., the quinone moiety vs. the Au(I)—NHC subunit), positively charged complexes containing a naphthoquinone (4[H][Cl]) and the [(NHC)$_2$Au]$^+$ core (5) were also studied; which provided IC$_{50}$ values of 0.99±0.12 μM and 0.71±0.06 μM, respectively. Improved antiproliferative activity (IC$_{50}$=0.197±0.057 μM) was observed when A549 cells were exposed to a combination of 4[H] [Cl] and 5 in a 2:1 molar ratio that matches their stoichiometric ratio in 1. However, this combination was not as effective as complex 1 (by a factor of 2.7).

Further anti-proliferation studies were carried out with complex 1 and its naphthoquinone component 4[H][Cl] using the following cell lines: A2780 ovarian (a wt-p53 cell line sensitive to platinum treatment), 2780CP ovarian (isogenic to A2780 but expressing multi-drug resistance (MDR)), and PC-3 prostate (p53 null) (Table 3). While both complexes reduced proliferation in all three cell lines, complex 1 was found to be statistically more potent in each cell line relative to 4[H][Cl].

TABLE 3

IC$_{50}$ values of the naphthoquinone Au(I)—NHC complex 1 and the naphthoquinone imidazolium salt 4[H][Cl] in various cancer cell lines.[a]

| Compound | A549 Lung | A2780 Ovarian | 2780CP Ovarian | PC-3 Prostate |
|---|---|---|---|---|
| 1[b,c] | 0.073 ± 0.016 | 0.026 ± 0.007 | 0.054 ± 0.006 | 0.096 ± 0.017 |
| 4[H][Cl][d] | 0.994 ± 0.120 | 0.159 ± 0.058 | 0.626 ± 0.117 | 0.136 ± 0.020 |

[a]Error is represented as standard error from the mean.
[b]Students t-test (unpaired) revealed 1 was significantly more potent than 4[H][Cl] in every cell line (p-value <0.005 for A549, A2780, 2780CP; p-value <0.05 for PC-3).
[c]Students t-test (unpaired) revealed that the potency was different in A2780.
[d]Students t-test (unpaired) revealed no difference in potency between the A2780 and PC3 cell lines. 2780CP was significantly different from A549, A2780, and PC-3 (p-value <0.0005).

Additional cell proliferation studies were carried out with a silver analog of compound 3 shown below:

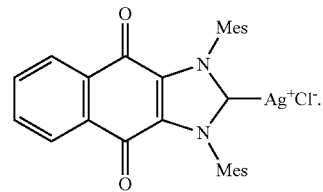

Figure 16:
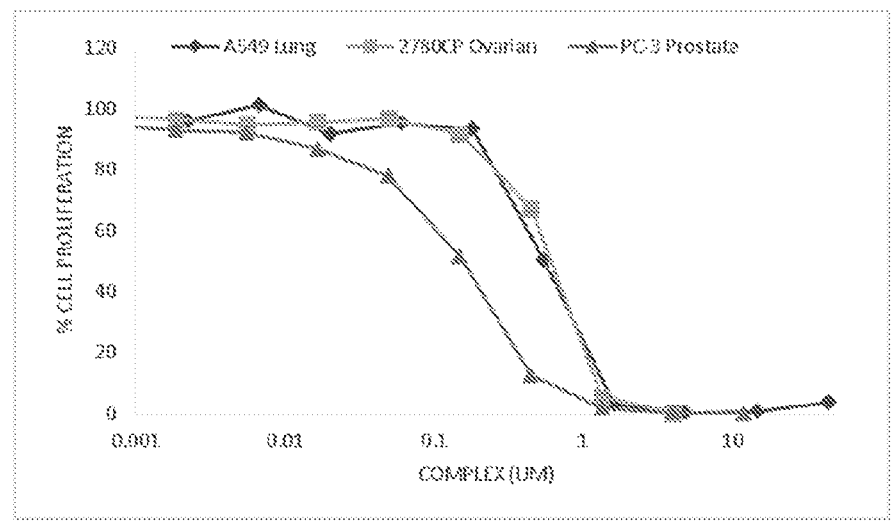
FIG. 16 shows the cell proliferation assay of a silver carbene derivative of compound 3. The concentration of the compound is shown in μM.

Results of this assay can be seen in FIG. 16.

D. Cellular Uptake and Interaction with Serum Proteins

Figure 3A:
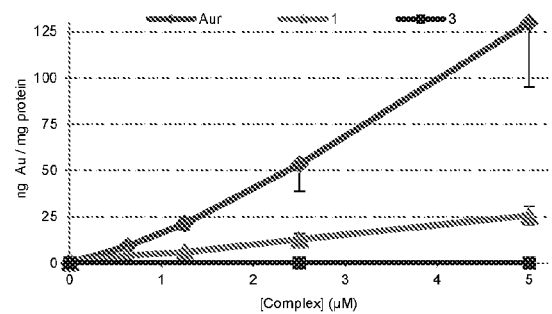
FIGS. 3A & 3B show ICP-MS detection of intracellular Au levels as an indicator of complex uptake into A549 lung cancer cells (FIG. 3A). Students t-test (unpaired) of 1 (2.5 μM) compared to auranofin (2.5 μM) provided p-value<0.05, indicating statistical significance. A comparison of 1 to 3 (p-value>0.2) revealed no statistical significance. Percent of free Au (non-protein bound) within samples of fetal bovine serum treated with 25 μM 1, 3, and auranofin (FIG. 3B). Error bars represent the standard error from the mean.
Figure 10:
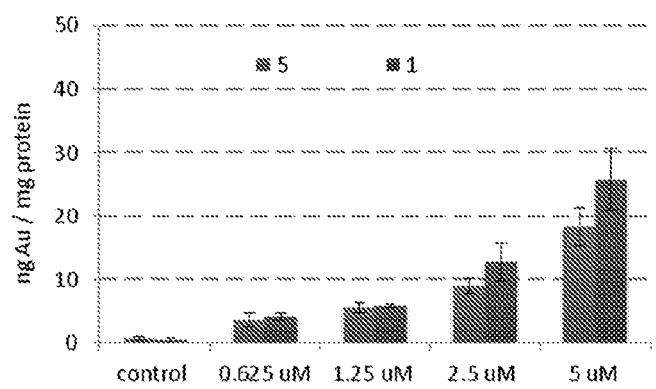
FIG. 10 shows the ICP-MS detection of intracellular Au uptake in A549 cells treated in 1 and 5. Students t-test (unpaired) of 1 (2.5 μM) compared to 5 (2.5 μM) provided p-value>0.2 suggesting no statistical significance. Error bars represent SEM.

To quantify the extent to which variations in cellular uptake might account for the differences in anti-proliferative efficacy seen for the various gold(I) complexes of this study, inductively coupled plasma mass spectrometry (ICP-MS) was used to detect intracellular Au levels (FIG. 3A). In brief, cell cultures of A549 were treated with varying doses of 1, 3, 5, and auranofin, collected and digested, and quantitatively assessed for intracellular Au content. It was found that regardless of dose, a 2-5 fold increase in intracellular Au concentrations was seen in samples treated with auranofin as compared to complex 1. In the case of 3, a neutral complex, no intracellular Au was detected under conditions identical to those used to test complex 1. The intracellular Au levels were found to be identical in the case of complexes 1 and 5 (FIG. 10).

Figure 3B:
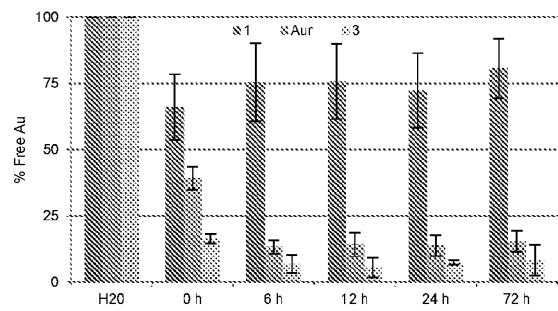

To assess potential drug protein interactions, samples of fetal bovine serum (FBS) were treated with 25 μM 1, 3, and auranofin prior to incubating at 37° C. Aliquots were taken and the free Au (non-protein bound, methanolic extracts)

content was analyzed by ICP-MS (FIG. 3B). As expected, the free Au content in the FBS samples treated with auranofin decreased in a time dependent manner (Iqbal et al., 2009; Roberts et al., 1996). A similar reduction in free Au was observed for FBS samples treated with complex 3. In contrast, minimal changes in the free Au levels were seen as a function of time in the samples containing complex 1. This result is consistent with the notion that Au(I)—NHC 1 enters the cell via different mechanism than auranofin (FIG. 3A). In addition, the protein binding differences between 1 and 3 could explain the relatively reduced potency seen in the case of 3.

E. Accentuation of Reactive Oxygen Species (ROS)

Figure 4A:
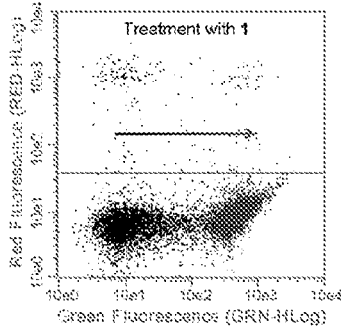
FIGS. 4A-4D show A549 cell population shift (black=vehicle treatment, red=treatment with 2.5 μM 1) indicating accentuation of intracellular ROS via flow cytometry (FIG. 4A). Dose responsive cell population shift of A549 cells treated with 1 (FIG. 4B). Dose responsive accentuation of intracellular ROS with various complexes post 6 hr incubation (FIG. 4C). Error bars represent the standard error of the mean. Treatment of A549 cells with 100 μM $H_2O_2$ was used as a positive control. Students t-test (unpaired) of 1 compared to the cocktail provided p-values>0.05 suggesting no statistical significance. Comparison of 1 to either 4[H][Cl] or 5 individually (p-values<0.005) revealed a statistically significant difference in both cases. A549 cancer cells stained to show ROS accentuation, mitochondria, and nuclei were treated with DMSO as vehicle and Complex 1. Fluoresent images of these cells are shown in FIG. 4D.
Figure 4B:
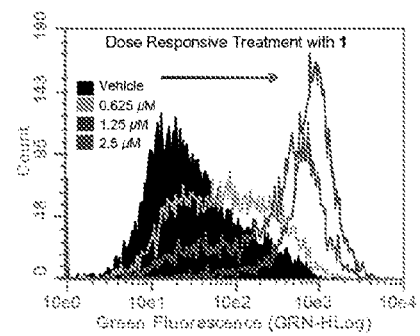
Figure 4C:
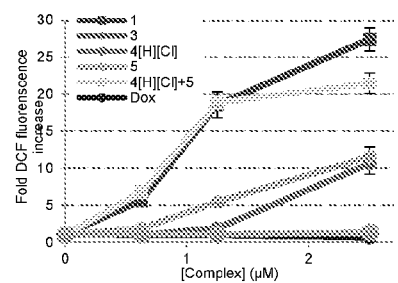
Figure 11:
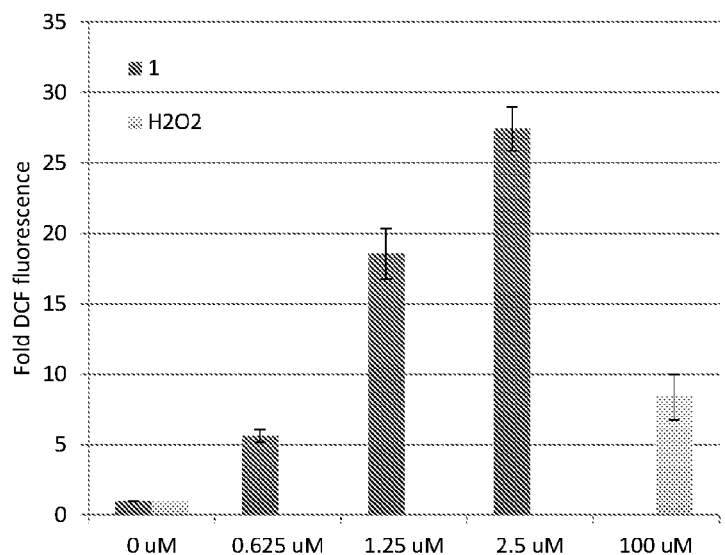
FIG. 11 shows the dose responsive accentuation of intracellular ROS with 1 post 6 h incubation. Error bars represent SEM. A549 treatment with 100 μM $H_2O_2$ was used as a positive control.

To establish whether or not the complexes of this disclosure would increase intracellular ROS levels, A549 cells were treated with each complex in a dose responsive manner. ROS fluctuations were monitored post treatment via flow cytometry using the fluorescein-based general ROS indicator (5-(and-6)-chloromethyl-2',7'-dichlorodihydrofuorescein diacetate, acetyl ester (CM-$H_2$DCFDA). Following treatment with 2.5 µM 1, a 27-fold fluorescence associated cell population shift was observed (FIG. 4A), a finding taken as indicative of a significant increase in intracellular ROS in the case of this complex. A dose dependence was also seen (FIG. 4B and FIG. 11). Upon treatment with the individual components of 1 (i.e. 4[H][Cl] and 5), a more modest increase in ROS was observed (~11-fold increase at the 2.5 µM dose level in each case), while minimal or no ROS increase was observed in the case of 3, auranofin, or doxorubicin (FIG. 4C). When A549 cells were exposed to a 2:1 molar ratio of 4[H] [Cl] and 5 a dose-dependent increase in ROS was observed that statistically similar to that produced by 1. This is rationalized in terms of the ROS enhancement produced upon exposure to the individual components present in 1 being additive and not synergistic.

Figure 4D:
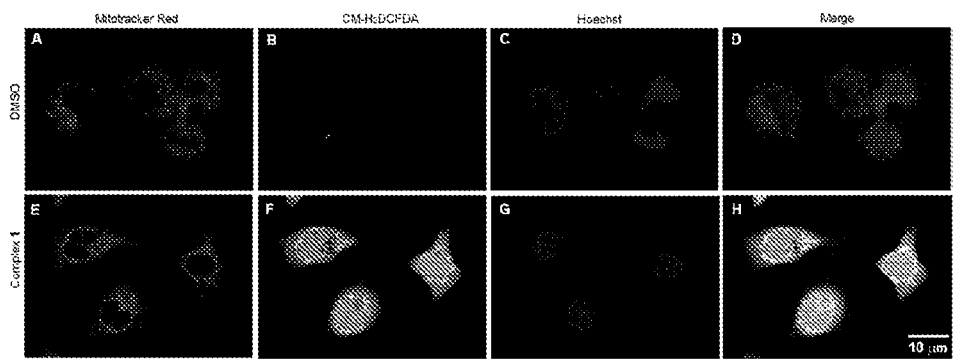

To further elucidate the subcellular loci of ROS accentuation, confocal microscopy was employed to fluorescently image A549 cancer cells treated with vehicle (DMSO) and 1.25 µM complex 1 (cf. FIG. 4D). All cells were selectively stained for visualization of ROS accentuation (green, CM-$H_2$DCFDA), mitochondria (red, Mitotracker Red), and nuclei (blue, Hoechst). No ROS accentuation was observed in cells treated with DMSO. A549 cells treated with complex 1 resulted in a general green fluorescence increase with localized areas of higher green fluorescence (cf. FIG. 4D, image F). Once merged, evident overlap of localized ROS accentuation with mitochondria (red) suggests that ROS accentuation is arising from mitochondria (cf. FIG. 4D, image H).

F. Inhibition of Thioredoxin Reductase

Figure 5A:
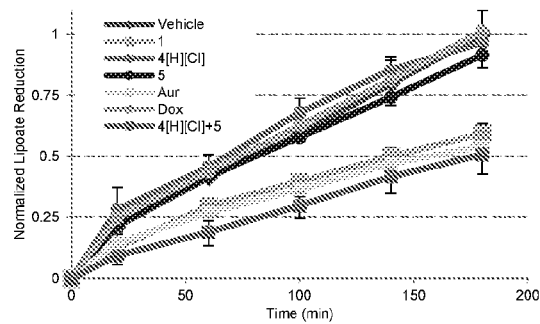
FIGS. 5A & 5B show time dependent inhibition of TrxR activity in A549 cells treated with 0.6125 μM of the indicated compound for 180 min (FIG. 5A). Complex 1 was statistically different than vehicle, 4[H] [Cl], 5, and Dox (p values<0.005), and similar to auranofin and 4[H][Cl]+5 (p values>0.1) by the (unpaired) Students t-test.
Figure 5B:
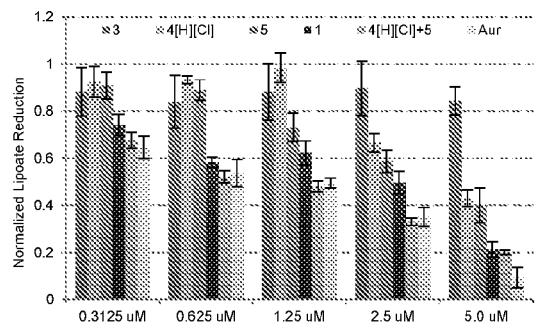
Figure 12A:
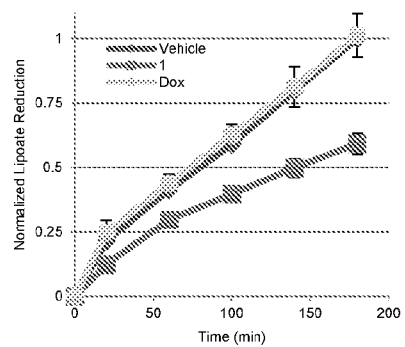
FIGS. 12A & 12B show the activity of TrxR as assessed by the detection of lipoate reduction. Comparison in TrxR activity in A549 cells treated with 1 and doxorubicin indicates a time (FIG. 12A) and dose (FIG. 12B) dependent inhibition of enzyme activity by 1 whereas no inhibition of activity in the presence of doxorubicin was detected. Error bars represent SEM.
Figure 12B:
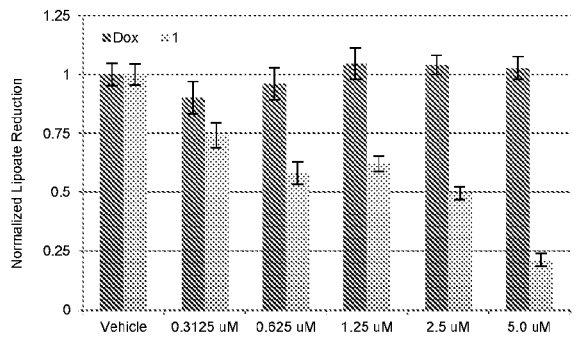

To assess whether any or all of the present gold complexes could serve as TrxR inhibitors, standard tests involving the reduction of the oxidized form of the cell-permeable cofactor lipoate to its corresponding reduced form, dihydrolipoate, were carried out. Briefly, plateau phase A549 cells were exposed to variable doses of complexes 1, 3, 4[H][Cl], a 2:1 molar ratio of 4[H] [Cl] and 5 (cocktail), auranofin, and doxorubicin for 6 h. Post treatment, the live cells were monitored colorimetrically over 180 min for their ability to reduce lipoate (FIG. 5A). Depending on the incubation concentration distinct differences in the time dependent inhibition of TrxR are evident. At low concentrations (0.1-0.6 µM), inhibition of TrxR was apparent in A549 cells exposed to 1, auranofin, and 4[H][Cl]+5, while little to no inhibition was seen in the case of 3-5 or doxorubicin. At higher concentrations (1.25-5.0 µM), inhibition of TrxR by 4[H][Cl] and 5 became evident, while 3 or doxorubicin remained inactive over the full concentration range used in the study (FIG. 12). Without wishing to be bound by any theory, it is believed that complex 1 will be able to act as both a TrxR inhibitor and a general agonist of oxidative stress.

G. Induction of Apoptosis

Figure 6:
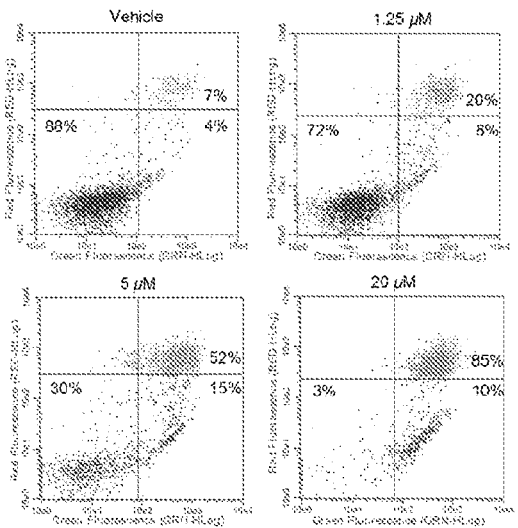
FIG. 6 shows cell death via apoptosis as detected using flow cytometry. Study is suggestive of the activation of apoptosis by 1 due to the presence of two separate annexin-V positive populations representing early stage (bottom right) and late stage (top right) apoptosis.
Figures 13A, 13B:
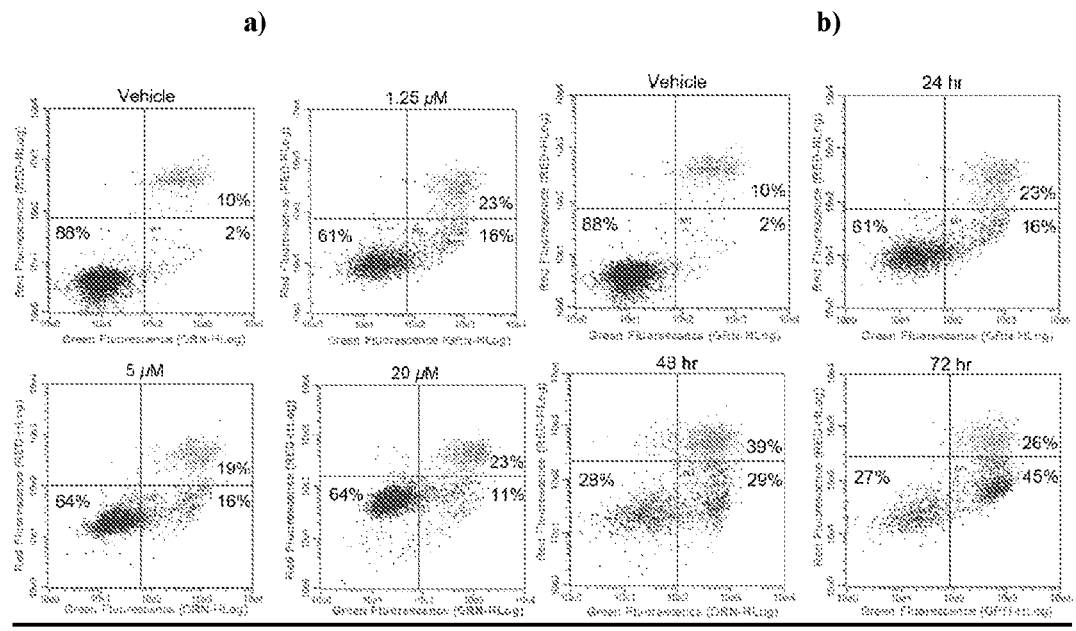
FIGS. 13A & 13B show (FIG. 13A) dose dependent induction of apoptosis in A549 cells treated with doxorubicin for 24 h and (FIG. 13B) time dependent induction of apoptosis in A549 cells treated with 1.25 μM doxorubicin.

To determine whether complex 1 also promotes apoptosis, flow cytometry studies in conjunction with annexin-V staining were carried out. In brief, plated exponential growth phase A549 cells were exposed to various concentrations of 1 and incubated for 24 h. At that point, all cells (adhered and floating) were collected, washed, and stained with fluorescein-labeled annexin-V and propidium iodide (PI) and subjected to flow cytometry (FIG. 6). At low doses, evidence of early stage apoptosis was seen, as inferred from the binding of annexin-V to the still-intact and impermeable cell membrane (resulting in FITC-only fluorescence). As the dose escalation progressed, a larger percentage of late stage apoptosis/necrotic (FITC positive and PI positive from staining of nuclear material) cells became evident. Treatment of A549 cells with doxorubicin (a known inducer of apoptosis) provided similar results in both the early and late stage apoptotic quadrants (FIGS. 13A & 13B). On this basis the evidence suggests that complex 1 induces controlled cell death via an apoptotic mechanism (Poornima et al., 2014).

H. Toxicity and Efficacy Studies in Zebrafish

Figures 7A, 7B, 7C, 7D, 7E, 7F, 7G, 7H:
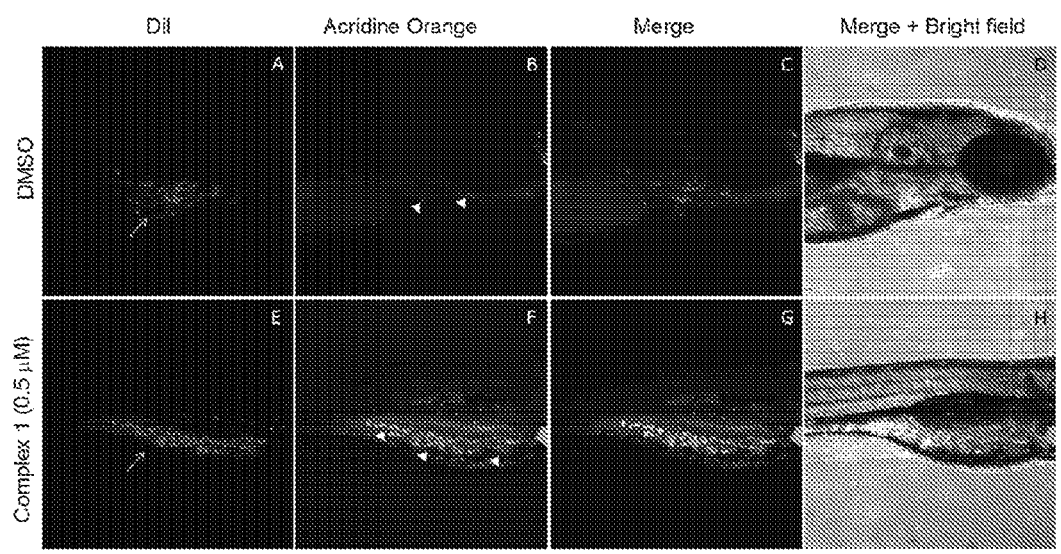
FIGS. 7A-7H show complex 1 induces tumor specific cell death in Zebrafish tumor xenografts.
Figure 14:
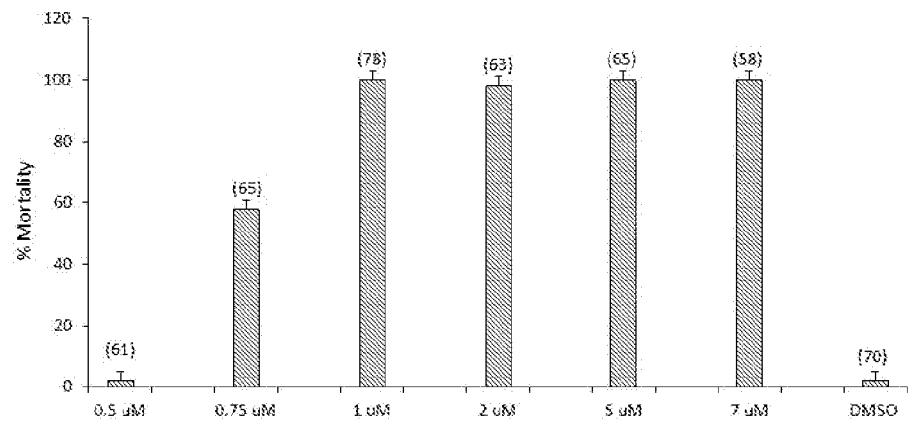
FIG. 14 shows the toxicity analysis of Complex 1 in Zebrafish larvae. Two-day old zebrafish larvae were treated with various doses of Complex 1 and DMSO for 24-48 hours. After treatment, the larvae were analyzed for mortality and percent mortality for each treatment group is quantified and graphed. Each treatment was done three times and the total number of larvae treated per dose is indicated within parenthesis above the respective bars. The 0.75 μM dose of complex 1 induces ~50% mortality in the and is identified as the $LD_{50}$ for zebrafish larvae. The 0.5 μM dose is identified as the Maximum Tolerated Dose (MTD). All these treatment groups are statistically significant from the control treatment (p<0.001, T-test).

The anticancer activity of the complex 1 was tested using a qualitative high throughput zebrafish tumor xenograft model (Sittaramane et al., 2015). First, zebrafish embryos were divided into 7 groups at an average of 65 embryos per group. Each group was treated with vehicle (DMSO) or complex 1 at variable concentrations to identify the maximum tolerable dose (MTD) (FIG. 14). A dosing of 0.5 µM was found to induce no observable toxic effect relative to vehicle (p-value>0.1) and was deemed to be the MTD for zebrafish embryos. Therefore, efficacy studies, using zebrafish bearing human tumor xenografts were carried out with complex 1 being administered at the 0.5 µM concentration level (Jung et al., 2012; Konantz et al., 2012; Tucker and Lardelli, 2007). Briefly, live human lung cancer cells (A549) were labeled with CM-DiI (red) and only live cells were transplanted via injection into the perivitelline space of 30 zebrafish embryos 24 hours post fertilization (hpf) (Sittaramane et al., 2015; Veinotte et al., 2014; Xie et al., 2015). Tumor inoculated zebrafish embryos were allowed to grow for one day till 48 hpf. This allows for establishment of the cancer cells in the host zebrafish embryos. At 48 hpf, the xenograft bearing zebrafish embryos were split into 2 groups (15 embryos per group) and treated with vehicle (DMSO) or complex 1 at 0.5 µM for one additional day (72 hpf), and cancer cell death was observed using acridine orange staining (green). Live zebrafish-A549 tumor xenografts treated with DMSO display features consistent with the presence of tumor cells (red, white arrows in FIG. 7A). On the other hand, few, if any, tumors and little evidence of host cell apoptosis was seen with acridine orange staining (green, arrowhead in FIGS. 7B-7D). Finally, live zebrafish-A549 tumor xenografts (red, white arrows in FIG. 7D) treated with complex 1 showed evidence of apoptosis for the majority of tumor cells under conditions of acridine orange staining (arrowhead in FIG. 7E and bright cells in FIGS. 7F & 7G).

I. Activity of Compounds 1 and 2

Figure 15A:
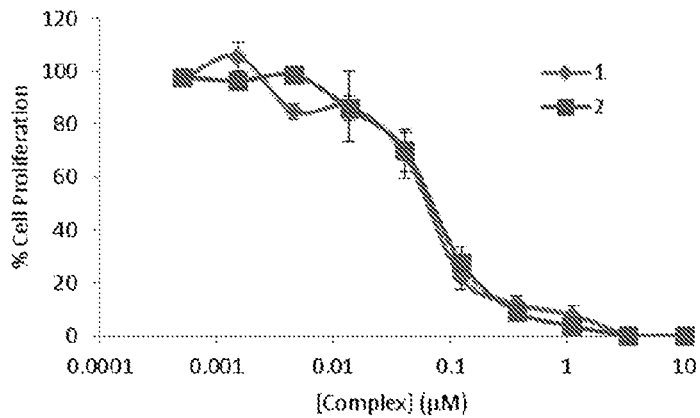
FIGS. 15A-15E shows (FIG. 15A) the average percent proliferation of A549 cells exposed to either 1 or 2 for 72 h at varying concentrations. Error bars represent SEM.
Figure 15B:
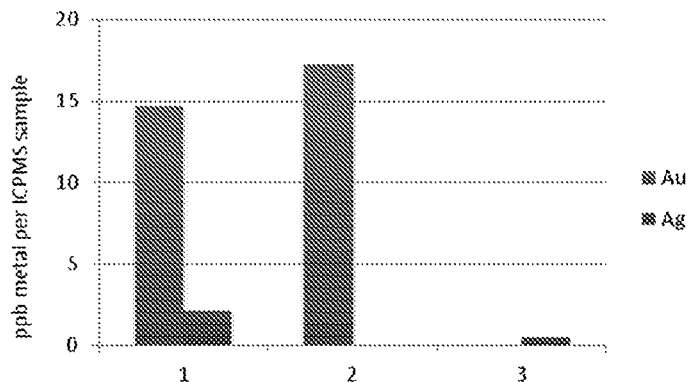
Figure 15C:
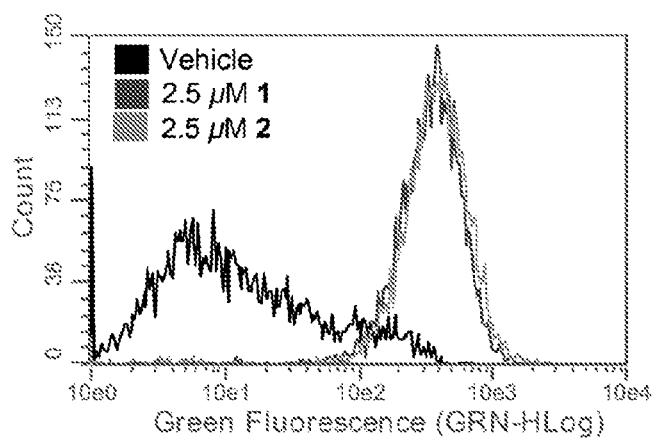
Figure 15D:
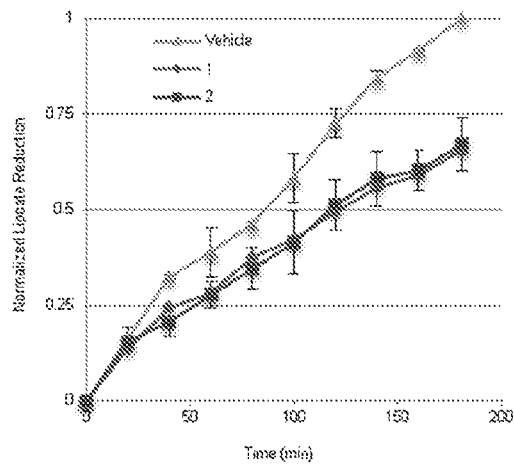
Figure 15E:
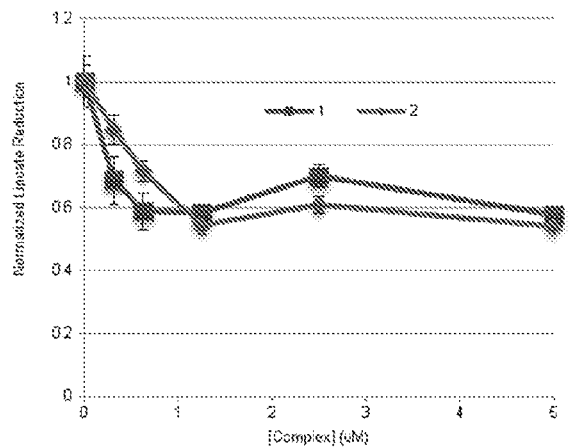

The activity of compound 1 was compared to the activity of compound 2 in the proliferation assay (FIG. 15A), the gold uptake assay (FIG. 15B), the generation of ROS in cells (FIG. 15C), and the reduction of lipoate both time dependent (FIG. 15D) and normalized (FIG. 15E). In these assays, the compounds performed similarly although the gold uptake assay also measured the presence of silver and showed roughly 7:1 ratio of gold to silver taken up by the cell suggesting that the silver cation does not enter the cell.

J. Materials and Methods i. Compound Synthesis 1,3-Dimesitylnapthoquinimidazolium chloride (Sanderson et al., 2006; Tennyson et al., 2010), (1,3-dimesityl-4,5-naphthoquino-imidazol-2-ylidene)-silver(I) chloride (Sanderson et al., 2006; Tennyson et al., 2010), $(C_4H_2S)AuCl$ (Hashmi, et al., 2010) were prepared according to the literature procedures. All other reagents were purchased from commercial sources and used as received, including: $[((CH_3)_3Si)_2N]Na$ (NaHMDS) and silver(I) oxide. $CD_2Cl_2$ (99.9%) was purchased from Acros Laboratories in glass ampules and used as received. Solvents were either dried with a solvent purification system from the Inert Innovative Technology, Inc. (dichloromethane, diethyl ether, hexanes, tetrahydrofuran and toluene) or freshly distilled over 3 Å molecular sieves and degassed using three consecutive freeze-pump-thaw cycles prior to use. UV-vis spectra were obtained at ambient temperature with a Hewlett-Packard 8452A diode array spectrophotometer with molar absorptivities reported in $M^{-1}$ $cm^{-1}$. $^1H$ and $^{13}C$ NMR spectra were recorded on Bruker 300 MHz spectrometer. Spectra were referenced to the residual solvent as an internal standard, for $^1H$ NMR: $CD_2Cl_2$, 5.32 ppm and $^{13}C$ NMR: $CD_2Cl_2$, 53.84 ppm. High-resolution mass spectra (HRMS) were obtained with an Agilent Technologies 6530 Accurate Mass Q-TOF LC/MS (ESI) and are reported as m/z (relative intensity). Electroanalytical measurements were performed on a CHI620E electrochemical workstation using a silver wire quasi-reference electrode, a platinum disk working electrode and a Pt wire auxiliary electrode in a three-electrode cell under an atmosphere of nitrogen. The electrochemical measurements were performed using 1.0 mM solutions of the analyte in dry DMSO with 0.1 M $[N(nBu)_4][PF_6]$ as the electrolyte and ferrocene (Fc) as the internal standard. Differential pulse voltammetry measurements were performed with 50 mV pulse amplitudes and 2 mV data intervals. All potentials listed herein were determined by differential pulse voltammetry and referenced to a saturated calomel electrode (SCE) by shifting ferrocene$^{0/+}$ to 0.435 V (DMSO) (Aranzaes et al., 2006). Spectroelectrochemistry measurements were obtained at ambient temperature with a custom designed three-electrode cell using Hewlett-Packard 8452A diode array spectrophotometer and CHI620E. Elemental analyses were performed by Midwest Microlab, LLC in Indianapolis, Ind. Cell culture media consisted of RPMI 1640 with 2 mM glutamine and 25 mM HEPES (Corning 10041CV) with 10% heat-inactivated fetal bovine serum (Sigma f6178) and 1× penicillin-streptomycin (Sigma p4333). Trypsin (Hyclone SH30236.01) and Dulbecco's Phosphate Buffer Saline (Sigma R5886) were used for general cell maintenance and harvesting. Cell lines were obtained from the ATCC (A549 and PC-3) and Prof. Zahid Siddik at MD Anderson (A2780 and A2780CP). Thiazolyl blue tetrazolium bromide (Alfa Aesar L11939) was used for cell proliferation assays. Cell culture plastic ware consisted of generic T-75 flasks, 80.5 mm diameter culture dishes, and treated 96-well plates.

ii. Experimental Compound Preparation.

Stock solutions of complexes 1-3, 4[H][Cl], auranofin (Tocris Bioscience 4600), and doxorubicin (Tocris Bioscience 2252) were dissolved in DMSO (2.5-10 mM, depending on the compound and its solubility), aliquoted, and stored at −80° C. prior to use.

iii. Biological Materials and Cell Lines.

Cell lines were obtained from the ATCC (A549 and PC-3) and Prof. Zahid Siddik at M.D. Anderson Cancer Center (A2780 and A2780CP). Cell culture plastic ware (i.e. T-75 flasks, treated 6-well plates, treated 96-well plates, and cell scrapers) were obtained from Fisher Scientific. Cell were cultured in RPMI 1640 culture medium (+2 mM glutamine, +25 mM HEPES, Corning 10041cv) supplemented with 10% heat-inactivated fetal bovine serum (RMBIO FBS-BBT) and 1× penicillin-streptomycin (Sigma p4333). Unless otherwise noted, incubators were set to 37° C. and 5% $CO_2$. Trypsin (HyClone SH30236.01) and 1× Phosphate Buffered Saline (HyClone SH30258.02, diluted in autoclaved deionized water) were utilized for general cell line maintenance and harvesting. Trace Metal Grade HCl (Fisher A508-4) and $HNO_3$ (Sigma 225711-475 mL) and autoclaved deionized water were used for studies involving ICP-MS. Diluent for samples and standards run on the ICP-MS was a 3% HCl solution made with the Trace Metal Grade HCl and autoclaved deionized water. The activity of thioredoxin reductase was monitored in live cells using a solution of lipoate (Tokyo Chemical Industry Co., Ltd. L0207) and DTNB (Acros Organics 117540050) in 1×HBSS (Life tech 14025-092).

iv. Cell Proliferation Studies.

Cells were harvested and seeded into 96-well culture plates (Costar 07-200-90) in 100 µL of culture media. They were allowed to incubate overnight at 37° C. in the presence of 5% $CO_2$. A549 was seeded at a density of 1000 cells/well, A2780 at 2500 cells/well, A2780CP at 3000 cells/well, and PC-3 at 2000 cells/well. The next day, appropriate serial dilutions of drug stocks in culture media were made. To each well of a 96 well plate was added 100 µL of the appropriate solution. After a total of three days, a 50 mL aliquot of 3 mg/mL tetrazolium dye, 344,5-dimethylthiazol-2-yl)-2,5-diphenyltetrazolium bromide (Alfa Aesar L11939) was added to each well, followed by a 4 hr incubation period at 37° C. The medium was then removed, the resulting formazan was dissolved in 50 mL DMSO and the respective absorbances were measured at 560-650 nm using a microplate reader (Molecular Devices, Sunnyvale, Calif.). Absorbance values were corrected for background and then normalized to wells containing untreated cells to allow for plate-to-plate comparisons. The data are shown as mean inhibition of proliferation or growth as a percentage of control cells and are from 2-3 replicate experiments. Resulting dose response curves were subjected to linear regression analysis (Origin by OriginLab, Inc.) for determination of $IC_{50}$ values.

v. ICP-MS Analysis and Preparations.

Roughly 7–8×10$^6$ cells were grown to 70-80% confluence in T-75 cell culture flasks (Thermo 130190) and treated with respective compound in RPMI medium supplemented with 10% FBS and antibiotics for the desired incubation time. The medium was then removed and cells were washed with 8 mL 1× warm PBS. 2 mL 1×PBS was then added to each flask, and the cells were removed by scraping. Each cell suspension was then pipetted into a clean, labeled 15 mL centrifuge tube (Thermo 339650). Cells were pelleted by centrifuging at 1,000 rpm for 5 min in an Eppendorf 5804 with a swing-bucket rotor. The supernatant was removed by vacuum aspiration, and the pellet was resuspended in 50 µL autoclaved deionized water. Suspension/lysates were then kept at −80° C. until further use. After thawing, the lysates were then sonicated using a Branson Digital Sonifier, and 5

µL aliquots were taken for determination of protein content of the sample. Lysates were digested with 80 µL aqua regia and heated to 65° C. for 1 h. Digested lysates were diluted with 4 mL 3% Trace Metal Grade HCl and gold content was measured on a Perkin Elmer NexION 300x set to detect gold at 197 m/z. Gold concentrations were quantified using the linear range of a standard curve generated by serial dilution of an ICP-MS gold standard (Ricca MSAU1KH-100) in 3% HCl. Values were then normalized to protein content as determined using a Modified Lowry Protein Assay Kit (Thermo 23240) and known concentrations of bovine serum albumin (Fisher 9048-46-8).

The Modified Lowry Assay was used to determine the protein content of each sample for normalization purposes. The standard curve for each run was made from a 2-fold serial dilution of fresh 5 mg/mL BSA solution. Aliquots were diluted to within the linear range of the standard curve using autoclaved DI water, and subjected to the Modified Lowry Assay in round-bottomed 96-well clear plates (Fisher 12565500). Each well contained 10 µL of sample, 50 µL of Modified Lowry Reagent, and 5 µL of 1 N Folin-Ciocalteau Reagent. All other aspects of the procedure were as detailed in the microplate procedure instructions that come with the kit.

vi. Serum Protein Binding Studies.

The binding of gold from each compound to proteins in non-heat inactivated fetal bovine serum (HyClone SH30910.02) was observed during a time-dependent study. A 25 µM solution of each compound in 3 mL warm FBS was made. The solutions were kept at 37° C. Over time, 100 µL aliquots of each solution were taken and precipitated into 400 µL cold methanol. Precipitated aliquots were stored at −80° C. The methanolic suspensions were then centrifuged at 11,000 rcf for 5 min in an Edvotek microcentrifuge. The supernatants were pipetted into new microcentrifuge tubes. Samples were prepared for ICP-MS by adding 200 µL supernatant from each sample to 2 mL 3% Trace Metal Grade HCl. Time points were at addition of compound (T0), 4, 6.25, 9.75, 12, 24, 48, 72, and 100 h.

vii. Detection of ROS by Flow Cytometry.

Tumor cells ($1 \times 10^6$) were plated in a 6-well plate overnight and then incubated with media containing various complexes described at concentrations of 0.625-2.5 µM. Control cells were treated with vehicle only. After a 6 h. incubation, the cells were washed with PBS, detached with 0.250 mL 1× trypsin, collected in a 15 mL conical tube, and pelleted by centrifugation (3 min @ 300 g) at 5° C. The resulting pellet was again washed 2× with cold PBS and pelleted at 5° C. The pellet was then suspended in freshly prepared 2 µM CM-H$_2$DCFDA (Lifetech C6827) in PBS for a final cell concentration of $1 \times 10^6$ cells/mL and incubated in the dark at 37° C. for 15 min. The cells were then pelleted, washed with 2 mL PBS, and re-suspended in PBS containing 2 µg/mL propidium iodide (PI, Chemodex P0023) for a final cell concentration of $0.5 \times 10^6$ cells/mL. Control samples of unstained cells, cells stained with only CM-H$_2$DCFDA, and cells stained with only PI were also prepared. Each sample was added to one well of a 96-well plate. Samples were then subjected to FACS analysis using a Millipore Guava easyCyte 8 and analyzed using the Guava inCyte software.

viii. Fluorescence Microscopy.

Tumor cells were harvested and seeded at a density of $2 \times 10^5$ cells/dish in 35 mm dishes containing a poly-D lysine coated 10 mm glass diameter (Mat Tek P35GC-1.5-10-C) overnight. Cells were then incubated with 1.25 µM complex at 37° C. 4 h. Post incubation, the media was removed and cells were washed (2×) with PBS. Cells were then incubated with 1 µM CM-H$_2$DCFDA (Lifetech C6827) in PBS at 37° C. for 15 min. The dye-PBS solution was removed and cells were washed with PBS (2×). To the cells was added a PBS solution containing 1 ug/mL Hoechst 33342 (Lifetech H1399) and 50 nM Mitotracker Red FM (Lifetech M22425) for 30 min at 37° C. After incubation, the dye-PBS solution was removed and cells were washed with PBS (2×). Cells were then imaged fluorescently on a Leica SP5 X White light laser confocal microscope. Images were taken with a 63×, NA 1.4 objective.

ix. Lipoate Inhibition Assays.

Cells were harvested and seeded at a density of 10,000 cells/well A549 in 96-well culture plates. They were then incubated overnight at 37° C. and 5% CO$_2$. The next day, appropriate serial dilutions of drug stock in culture media were performed, and 100 µL of the appropriate solution were added to each well. Cells were returned to the incubator for 6 h. Afterwards, the liquid was then removed from each well by vacuum aspiration and replaced by 100 µL of 5 mM lipoate (Tokyo Chemical Industry Co., Ltd. L0207) and 1 mM DTNB (Acros Organics 117540050) in HBSS (Life tech 14025-092). The absorbance of each well at 605 nm was recorded immediately and once every 20 min for three h on a microplate reader (Molecular Devices, Sunnyvale, Calif.). Plates were covered with aluminum foil between readings.

x. Detection of Apoptosis.

Tumor cells ($2-3 \cdot 10^5$) were plated overnight and then incubated with media containing doxorubicin and 1 drug concentrations at 1.25-20 µM. Control cells were treated with vehicle only. At 24 h, the media was collected and the cells were washed with PBS. The PBS washing was collected and the attached cells were then subjected to 0.5× trypsin (diluted with PBS) for 2 min. All media and washings were collected, pelleted by centrifugation (3 min @ 300 g) and washed twice with cold PBS. The cells were once again pelleted and suspended in Annexin-V binding buffer (BD Biosciences 556547) at a final concentration of $1 \times 10^6$ cells/mL. After this, 100 µL of cell suspension was added to 1.5 mL centrifuge tubes, followed by 5 µL each of Annexin V-FITC and propidium iodide (PI, 50 µg/mL) solution. Control samples of unstained cells, cells stained with only Annexin V-FITC, and cells stained with only PI were also prepared. Samples were allowed to incubate in the dark for 15 min at ambient temperature. After incubation, each sample was diluted with 200 µL of Annexin V binding buffer, and the resulting 300 µL sample was added to one well of a 96-well plate. Samples were then subjected to FACS analysis using a Millipore Guava easyCyte 8 and analyzed using Guava inCyte software.

xi. Thermal Denaturation Studies.

Thermal denaturation studies were performed to determine the ability of 1, 4[H][Cl], and doxorubicin to bind a DNA duplex (5'CCGCAGCCA3'/5'TGGCTGCGG3', Integrated DNA Technologies). Stock solutions of 1.6 mM DNA oligomer were prepared in TE buffer and stored at 5° C. To form the DNA duplex, equimolar aliquots of each DNA oligomer were combined and annealed at 95° C. for 5 min. The DNA sample was then placed on ice and briefly centrifuged to collect condensation. The DNA was aliquoted into separate 0.6 mL micro-centrifuge tubes and 1 molar equivalent of each 1, 4[H][Cl], and doxorubicin was added. To each sample, 12 µL of 1 mM EDTA, 12 µL of 100 mM NaCl, and 12 µL of 20 mM MOPS buffer (pH 7.4) were added and each sample was diluted to a total volume of 120 µL for a final complex and DNA duplex concentration of 5 µM. Samples were transferred to an 8 series microcell (1.0 cm path, 130 μL total volume). The absorbance of each sample was measured using a Shimadzu 2600 UV-vis spectrophotometer enabled with a thermal melt apparatus at a ramp rate of 1° C./min from 20° C. to 95° C. The melting temperature was determined mathematically (Origin by OriginLab, Inc.) by calculating the maximum of the first derivative of the sigmoidal melt curve.

xii. Zebrafish Toxicity Analysis.

To determine the maximum tolerable dose (MTD) for Complex 1, we performed zebrafish toxicity analysis (Sittaramane et al., 2015; He et al., 2010; Fako and Furgeson, 2009; Hill et al., 2005; Zhang et al., 2013; Heimberger et al., 2015). Briefly, wild-type zebrafish embryos were exposed to Complex 1 from 24 hpf (hours post fertilization) under standard conditions (Westerfield 2000). Embryos were allowed to grow till 3 dpf (days post fertilization) in 1 mL of solutions containing various concentrations complex 1. The embryonic development of zebrafish embryos was monitored at 48 hpf and 72 hpf to record the number of dead embryos. Complex 1 was dissolved in DMSO after purification and subsequently resuspended in E3 (embryonic medium) at various concentrations (FIG. 14) to assess toxicity in zebrafish embryos. Therefore, our controls were WT (wild-type) embryos in E3 with the same concentrations of DMSO as in complex 1 solutions. Lethality assay was performed at concentrations from 0.5 μM to 7 μM and these studies revealed that complex 1 has a $LD_{50}$ (50% lethal dose) of 0.75 μM. Our study identifies the Maximum Tolerable Dose (MTD) of complex 1 for zebrafish embryos is about 0.5 μM. Complex 1 displayed 100% lethality at concentrations above 1 μM (FIG. 14). Therefore, we performed all our tumor xenograft exposure assays at 0.5 μM concentrations.

Example 2—Activity of Calreticulin in Cells with Gold Carbene Complexes

Figure 17:
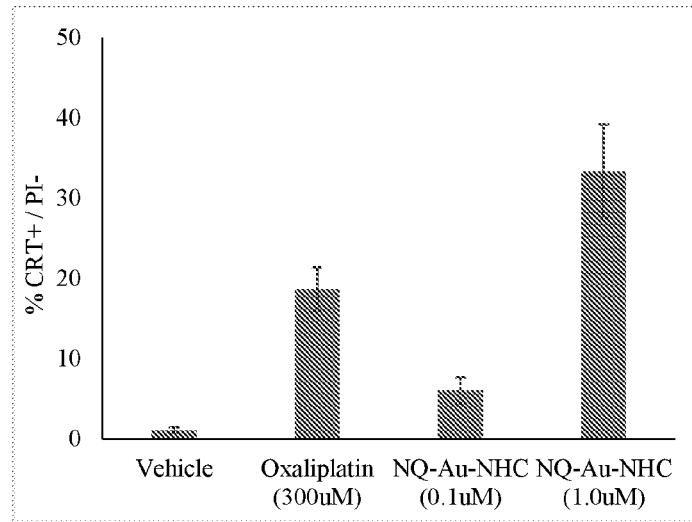
FIG. 17 shows the percentage of cells that express calreticulin on the surface of the cells after treatment with one or more therapeutic agent relative to the vehicle.

Compound 2 was tested for its ability to induce translocation of calreticulin (CRT) in Panc-02 cells compared to the similar activity of oxaliplatin. As shown in FIG. 17, oxaliplatin results in the presence of CRT on 18.6±2.8% of cells with 300 μM oxaliplatin while even 0.1 μM of 2 results in the presence of CRT in 6.1±1.6% of cells while 1.0 μM of 2 results in the presence of CRT in 33.4±5.8% of cells. These values were compared to vehicle which showed the presence of CRT in 1.1±0.4% of cells.

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Arambula et al., Chem. Sci., 7, 1245-1256, 2016.
Aranzaes et al., Can. J. Chem., 84 (2), 288-299, 2006.
Baker et al., Dalton Trans, DOI: 10.1039/b316804b, 1038-1047, 2004.
Baker et al., Dalton Trans, DOI: 10.1039/b602560a, 3708-3715, 2006.
de Fremont et al., Organometallics, 24, 2411-2418, 2005.
Fako and Furgeson, Adv. Drug Deliv. Rev., 61, 478, 2009.
Gomez et al., Electrochem. Commun., 5, 12-15, 2003.
Guth et al., International Journal of Electrochemistry, 2011, 22, 2011.
Handbook of Pharmaceutical Salts: Properties, and Use (P. H. Stahl & C. G. Wermuth eds., Verlag Helvetica Chimica Acta, 2002).
Hashmi, et al., Adv. Synth. Catal., 352 (8), 1315-1337, 2010.
He et al., Chem. Res. Toxicol. 26, 89, 2013.
Heimberger et al., Bioorg. Med. Chem. Lett., 25, 1191, 2015.
Hill et al., Toxicol. Sci., 86, 6, 2005.
Hu et al., Organometallics, 23, 755-764. 2004.
Iqbal et al., Biol. Trace Elem. Res., 130, 204-209, 2009.
Jung et al., Mol. Biosyst., 8, 1930-1939, 2012.
Konantz et al., Ann. N.Y. Acad. Sci., 1266, 124-137, 2012.
March's Advanced Organic Chemistry: Reactions, Mechanisms, and Structure, 2007.
Perez-Galan et al., Tetrahedron, 72, 3647-3652, 2016.
Poornima et al., Food Chem. Toxicol., 68, 87-98, 2014.
Roberts et al., 3rd, Inorg. Chem., 35, 424-433, 1996.
Sanderson et al., J. Am. Chem. Soc., 128 (51), 16514-16515, 2006.
Sanderson et al., J. Am. Chem. Soc., 128, 16514-16515, 2006.
Santoro et al., Dalton Trans, 45, 4970-4973, 2015.
Sittaramane et al., Chem. Med. Chem., 10 (11), 1802-7, 2015.
Sittaramane et al., ChemMedChem, 10, 1802-1807, 2015.
Stordal and Davey, IUBMB Life, 59(11):696-699, 2007.
Tennyson et al., J. Am. Chem. Soc., 132 (27), 9420-9429, 2010.
Tennyson et al., J. Am. Chem. Soc., 132, 9420-9429, 2010.
Tucker and Lardelli, Zebrafish, 4, 113-116, 2007.
Veinotte et al., Disease Models & amp; Mechanisms, 7, 745-754, 2014.
Wang and Lin, Organometallics, 17, 972-975, 1998.
Wang et al., J. Biol. Chem., 279, 25535-25543, 2004.
Westerfield, The Zebrafish Book. A Guide for the Laboratory Use of Zebrafish (Danio rerio), 4th ed.; University of Oregon Press: Eugene, 2000.
Xie et al., Future Med. Chem., 7, 1395-1405, 2015.
Zhang et al., Chem. Res. Toxicol., 26, 1168, 2013.

What is claimed is:

1. A compound of the formula:

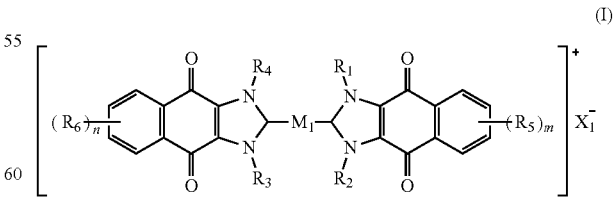

(I)

wherein:

$M_1$ is an Au or Ag ion;

$R_1$, $R_2$, $R_3$, and $R_4$ are each independently $alkyl_{(C \leq 12)}$, $aryl_{(C \leq 18)}$, or a substituted version of any of these groups;

R₅ and R₆ are each independently hydrogen, or alkyl$_{(C\leq12)}$, or a substituted version thereof;
m and n are each independently 1, 2, 3, or 4;
X₁ is Cl⁻, Br⁻, I⁻, PF₆⁻, BF₄⁻, OTf⁻, SbF₆⁻, AgCl₂⁻, ClO₄⁻, NO₃⁻, or H₃CC(O)O—.

2. The compound of claim 1 further defined as:

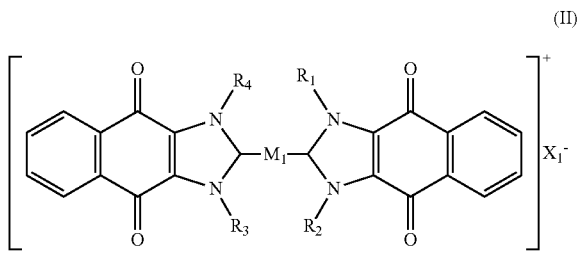
(II)

wherein:
  M₁ is an Au or Ag ion;
  R₁, R₂, R₃, and R₄ are each independently aryl$_{(C\leq18)}$, or a substituted version of any of these groups;
  X₁ is Cl⁻, Br⁻, I⁻, PF₆⁻, BF₄⁻, OTf⁻, SbF₆⁻, AgCl₂⁻, ClO₄⁻, NO₃⁻, or H₃CC(O)O—.

3. The compound of claim 1, wherein R₁ is aryl$_{(C\leq18)}$ or substituted aryl$_{(C\leq18)}$.

4. The compound of claim 1, wherein R₂ is aryl$_{(C\leq18)}$ or substituted aryl$_{(C\leq18)}$.

5. The compound of claim 1, wherein R₃ is aryl$_{(C\leq18)}$ or substituted aryl$_{(C\leq18)}$.

6. The compound of claim 1, wherein R₄ is aryl$_{(C\leq18)}$ or substituted aryl$_{(C\leq18)}$.

7. The compound of claim 1, wherein M₁ is an Au ion.

8. The compound of claim 1, wherein M₁ is an Ag ion.

9. The compound of claim 1, wherein X₁⁻ is Cl⁻ or AgCl₂⁻.

10. The compound of claim 1, wherein the compound is further defined as:

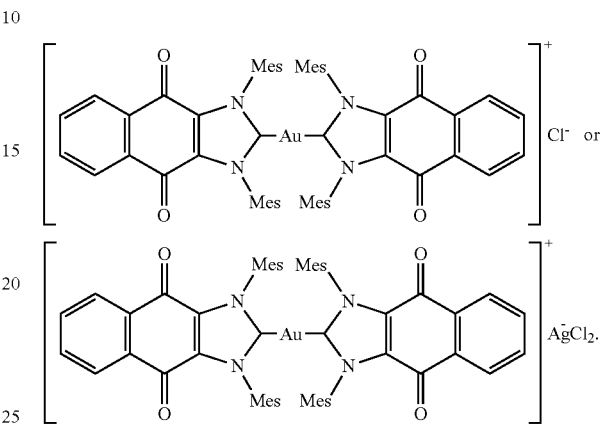

11. A pharmaceutical composition comprising:
  (A) a compound of claim 1; and
  (B) an excipient.

* * * * *